United States Patent [19]

Raddatz et al.

[11] Patent Number: 4,771,062
[45] Date of Patent: Sep. 13, 1988

[54] DIARYL SULPHIDE DERIVATIVES

[75] Inventors: Siegfried Raddatz, Cologne; Hans Plümpe, Wuppertal; Romanis Fruchtmann, Cologne; Christian Kohlsdorfer, Erfstadt; Bernhard Pelster, St. Augustin, all of Fed. Rep. of Germany

[73] Assignee: Bayer Aktiengesellschaft, Leverkusen, Fed. Rep. of Germany

[21] Appl. No.: 18,091

[22] Filed: Feb. 20, 1987

[30] Foreign Application Priority Data

Mar. 8, 1986 [DE] Fed. Rep. of Germany ....... 3607669
Sep. 20, 1986 [DE] Fed. Rep. of Germany ....... 3632042

[51] Int. Cl.$^4$ .................. C07D 277/42; A61K 31/425
[52] U.S. Cl. ................................ 514/370; 514/227.2; 544/53; 548/193
[58] Field of Search .......... 548/193; 544/53; 514/370, 226

[56] References Cited

U.S. PATENT DOCUMENTS 3,345,257 10/1967 Duerr ................. 514/370
3,804,848 4/1974 Behner ................ 548/193
3,860,590 1/1975 Wollweber ............ 548/193
4,297,490 10/1981 Newmann ............. 548/193
4,652,575 3/1987 Baglioni ............. 548/193

OTHER PUBLICATIONS

Chemical Abstracts, Band 98, Nr. 3, 17. Janner 1983, Columbus, Ohio, U.S.A., Damas, J.; Deflandre, E.; Bethegnies, G.; Gesquiere, J. C. "Prostaglandin Synthesis Inhibition by 2-[4-(Phenylthio)Phenylamino] Nicotinic Acids". Seite 26, Spalte 1, Zusammenfassung-Nr. 11192p & C. R. Seances Soc. Biol. Ses Fil. 1982, 176(4), 558-62.

Chemical Abstracts, Band 94, Nr. 3, 19. Janner 1981, Columbus, Ohio, U.S.A., Marcincal-Lefebvre, A.; Gesquiere, J. C.; B. Hegnies, G.; Dupuis, B.; Vincent, A.; Lemer, C. "2-[2-(Phenylthio)Phenylamino]Nicotinic Acids., and 2-[4-(Phenylthio)Phenylamino]Nicotinic Acids, Synthesis and Antiinflammatory Activity" Seite 421, Spalte 1, Zusammenfassung-Nr. 15515m & Ann. Pharm. Fr. 1980, 38(3), 243-52.

Primary Examiner—Robert Gersil
Attorney, Agent, or Firm—Sprung Horn Kramer & Woods

[57] ABSTRACT

A diaryl sulphide derivative of the formula (I)

in which $R^1$ represents a thiazolamino radical of the formulae wherein
$R^5$ represents hydrogen, alkyl, aralkyl or acyl,
$R^6$ and $R^{6'}$ are identical or different and represent hydrogen, alkyl, aralkyl or aryl,
$R^7$ represents alkyl, cycloalkyl, aralkyl, acyl or aryl and
n represents the number 1 or 2,
$R^2$ and $R^3$ are identical or different and represent hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represent a group of the formula $$-N\begin{matrix}R^8\\R^9\end{matrix}$$

wherein
$R^8$ and $R^9$ are identical or different and represent hydrogen, alkyl, aryl, aralkyl, acyl, trifluoroacetyl, alkylsulphonyl, arylsulphonyl, trifluoromethylphenylsulphonyl or tolylsulphonyl and
$R^4$ has one of the abovementioned meanings or $R^1$, or represents hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represents a group of the formula $$-N\begin{matrix}R^8\\R^9\end{matrix}$$

wherein
$R^8$ and $R^9$ have the abovementioned meanings, and salts thereof. Such diaryl sulphide derivatives being useful as active compounds in the treatment and prevention of diseases of the respiratory tract and cardiovascular diseases.

8 Claims, No Drawings

DIARYL SULPHIDE DERIVATIVES

BACKGROUND OF THE INVENTION

Field of the Invention

The invention relates to new diaryl sulphide derivatives, processes for their preparation and their use in medicaments.

SUMMARY OF THE INVENTION

Diaryl sulphide derivatives of the general formula (I)

$$R^1-\text{C}_6H_3(R^2)-S-\text{C}_6H_3(R^3)-R^4 \quad (I)$$

in which
$R^1$ represents a thiazolamino radical of the formulae

[structures showing four thiazolamino radicals with substituents $R^5$, $R^6$, $R^{6'}$, $R^7$, and $(CHR^{6'})_n-S$]

wherein
$R^5$ represents hydrogen, alkyl, aralkyl or acyl,
$R^6$ and $R^{6'}$ are identical or different and represent hydrogen, alkyl, aralkyl or aryl,
$R^7$ represents alkyl, cycloalkyl, aralkyl, aryl or acyl and
n represents the number 1 or 2,
$R^2$ and $R^3$ are identical or different and represent hydrogen, alkyl, alkenyl, cycloalkyl, alkylthio, alkoxy, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represent a group of the formula $$-N\begin{matrix}R^8\\R^9\end{matrix}$$

wherein
$R^8$ and $R^9$ are identical or different and represent hydrogen, alkyl, aryl, aralkyl, acyl, trifluoroacetyl, alkylsulphonyl, arylsulphonyl, trifluoromethylphenylsulphonyl or tolylsulphonyl and
$R^4$ has one of the abovementioned meanings of $R^1$, or represents hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represents a group of the formula $$-N\begin{matrix}R^8\\R^9\end{matrix}$$

wherein
$R^8$ and $R^9$ have the abovementioned meaning, and salts thereof, have been found.

DETAILED DESCRIPTION OF THE INVENTION

Alkyl here in general represents a straight-chain or branched hydrocarbon radical with 1 to 12 carbon atoms. Lower alkyl with 1 to about 8 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general represents a straight-chain or branched hydrocarbon radical with 2 to 12 carbon atoms and one or more, preferably with one or two, double bonds. A lower alkenyl radical with 2 to about 6 carbon atoms and one double bond is preferred. An alkenyl radical with 2 to 4 carbon atoms and one double bond is particularly preferred. Examples which may be mentioned are vinyl, allyl, propenyl, isopropenyl, butenyl, isobutenyl, pentenyl, isopentenyl, hexyl, isohexenyl, heptenyl, isoheptenyl, octenyl and isooctenyl.

Cycloalkyl in general represents a cyclic hydrocarbon radical with 5 to 8 carbon atoms. The cyclopentyl and the cyclohexyl radical are preferred. Cyclopentyl, cyclohexyl and cycloheptyl may be mentioned as examples.

Alkoxy in general represents a straight-chain or branched hydrocarbon radical which has 1 to 12 carbon atoms and is bonded via an oxygen atom. Lower alkoxy with 1 to about 6 carbon atoms is preferred. An alkoxy radical with 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general represents a straight-chain or branched hydrocarbon radical which has 1 to 12 carbon atoms and is bonded via a sulphur atom. Lower alkylthio with 1 to about 6 carbon atoms is preferred. An alkylthio radical with 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Halogenoalkyl in general represents straight-chain or branched lower alkyl with 1 to about 6 carbon atoms and one or more halogen atoms, preferably with one or more fluorine, chlorine and/or bromine atoms. Alkyl with 1 to 4 carbon atoms and with one or more fluorine and/or chlorine atoms is preferred. Alkyl with 1 or 2 carbon atoms and with up to five fluorine atoms or with up to three chlorine atoms is particularly preferred. Examples which may be mentioned are: fluoromethyl, chloromethyl, bromomethyl, fluoroethyl, chloroethyl, bromoethyl, fluoropropyl, chloropropyl, bromopropyl, fluorobutyl, chlorobutyl, bromobutyl, fluoroisopropyl, chloroisopropyl, bromoisopropyl, difluoromethyl, trifluoromethyl, dichloromethyl, trichloromethyl, difluoroethyl, dichloroethyl, trifluoroethyl, tetrafluoroethyl, pentafluoroethyl, trichloroethyl and trifluoropropyl. Trifluoromethyl, difluoromethyl, fluoromethyl, chloromethyl and trifluoroethyl are especially preferred.

Halogenoalkoxy in general represents a straight-chain or branched lower alkyl radical which has 1 to about 6 carbon atoms and one or more halogen atoms, preferably with one or more fluorine, chlorine and/or bromine atoms, and is bonded via an oxygen atom. Halogenoalkoxy with 1 to 4 carbon atoms and with one or more fluorine and/or chlorine atoms is preferred. Halogenoalkoxy with 1 or 2 carbon atoms and with up to 5 fluorine atoms or with up to 3 chlorine atoms is particularly preferred. Examples which may be mentioned are: fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, bromobutoxy, fluoroisopropoxy, chloroisopropoxy, bromoisopropoxy, difluoromethoxy, trifluoromethoxy, dichloromethoxy, trichloromethoxy, difluoroethoxy, trifluoroethoxy, tetrafluoroethoxy, pentafluoroethoxy, trichloroethoxy and trifluoropropoxy. Trifluoromethoxy, difluoromethoxy, fluoromethoxy, chloromethoxy and trifluoroethoxy are especially preferred.

Halogenoalkylthio in general represents a straight-chain or branched lower alkyl radical which has 1 to about 6 carbon atoms and one or more halogen atoms, preferably with one or more fluorine, chlorine and/or bromine atoms, and is bonded via a sulphur atom. Halogenoalkylthio with 1 to 4 carbon atoms and with one or more fluorine or chlorine atoms is preferred. Halogenoalkylthio with 1 or 2 carbon atoms and with up to five fluorine atoms or with up to 3 chlorine atoms is particularly preferred. Examples which may be mentioned are: fluoromethylthio, chloromethylthio, bromomethylthio, fluoroethylthio, chloroethylthio, bromoethylthio, fluoropropylthio, chloropropylthio, bromopropylthio, fluorobutylthio, bromobutylthio, chlorobutylthio, fluoroisopropylthio, chloroisopropylthio, bromoisopropylthio, difluoromethylthio, trifluoromethylthio, dichloromethylthio, trichloromethylthio, difluoroethylthio, trifluoroethylthio, tetrafluoroethylthio, pentafluoroethylthio, trichloroethylthio and trifluoropropylthio. Trifluoromethylthio, difluoromethylthio, fluoromethylthio, chloromethylthio and trifluoroethylthio are especially preferred.

Aryl in general represents an aromatic radical with 6 to about 12 carbon atoms. Preferred aryl radicals are phenyl, naphthyl and biphenyl.

Aralkyl in general represents an aryl radical which has 7 to 14 carbon atoms and is bonded via an alkylene chain. Aralkyl radicals with 1 to 6 carbon atoms in the aliphatic part and 6 to 12 carbon atoms in the aromatic part are preferred. The following aralkyl radicals may be mentioned as examples: benzyl, naphthylmethyl, phenethyl and phenylpropyl.

Aryloxy in general represents an aromatic radical which has 6 to about 12 carbon atoms and is bonded via an oxygen atom. Preferred aryloxy radicals are phenoxy or naphthyloxy.

Aralkoxy in general represents an aralkyl radical with 7 to 14 carbon atoms, the alkyl chain being bonded via an oxygen atom. Aralkoxy radicals with 1 to 6 carbon atoms in the aliphatic part and 6 to 12 carbon atoms in the aromatic part are preferred. The following aralkoxy radicals may be mentioned as examples: benzyloxy, naphthylmethoxy, phenethoxy and phenylpropoxy.

Aralkylthio in general represents an aralkyl radical with 7 to 14 carbon atoms, the alkyl chain being bonded via a sulphur atom. Aralkylthio radicals with 1 to 6 carbon atoms in the aliphatic part and 6 to 12 carbon atoms in the aromatic part are preferred. The following aralkylthio radicals may be mentioned as examples: benzylthio, naphthylmethylthio, phenethylthio and phenylpropylthio.

Acyl in general represents phenyl or straight-chain or branched lower alkyl with 1 to about 6 carbon atoms, which is bonded via a carbonyl group. Phenyl and alkyl radicals with up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Alkoxycarbonyl can be represented, for example, by the formula

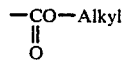

Alkyl here represents a straight-chain or branched hydrocarbon radical with 1 to 8 carbon atoms. Lower alkoxycarbonyl with 1 to about 6 carbon atoms in the alkyl part is preferred. An alkoxycarbonyl radical with 1 to 4 carbon atoms in the alkyl part is particularly preferred. The following alkoxycarbonyl radicals may be mentioned as examples: methoxycarbonyl, ethoxycarbonyl, propoxycarbonyl, isopropoxycarbonyl, butoxycarbonyl and isobutoxycarbonyl.

Carboxyalkyl in general represents a straight-chain or branched hydrocarbon radical which has 1 to 12 carbon atoms and is substituted by a carboxyl group. Carboxy-lower alkyl with 1 to about 6 carbon atoms is preferred. Examples which may be mentioned are: carboxymethyl, 1-carboxyethyl, 1-carboxypropyl, 1-carboxybutyl, 1-carboxypentyl, 1-carboxyhexyl, 2-carboxyethyl, 2-carboxypropyl, 2-carboxybutyl, 3-carboxypropyl, 3-carboxybutyl, 4-carboxybutyl, 2-carboxyl-1-propyl and 1-carboxy-1-propyl.

Alkoxycarbonylalkyl in general represents a straight-chain or branched hydrocarbon radical which has 1 to 12 carbon atoms and is substituted by an alkoxycarbonyl group, alkoxycarbonyl having the abovementioned meaning. Lower alkoxycarbonyl-lower alkyl with in each case 1 to about 6 carbon atoms in each alkyl part is preferred. Examples which may be mentioned are: methoxycarbonylmethyl, ethoxycarbonylmethyl, propoxycarbonylmethyl, butoxycarbonylmethyl, isopropoxycarbonylmethyl, isobutoxycarbonylmethyl, 1-methoxycarbonyl-ethyl, 1-ethoxycarbonyl-ethyl, 1-propoxycarbonyl-ethyl, 1-butoxycarbonyl-ethyl, 1-isopropoxycarbonyl-ethyl, 1-isobutoxycarbonyl-ethyl, 2-methoxycarbonyl-ethyl, 2-ethoxycarbonylethyl, 2-propoxycarbonyl-ethyl, 2-butoxycarbonyl-ethyl, 2-isopropoxycarbonyl-ethyl, 2-isobutoxycarbonyl-ethyl, 2-methoxycarbonyl-2-propyl, 2-ethoxycarbonyl-2-propyl, 2-propoxycarbonyl-2-propyl, 2-butoxycarbonyl-2-propyl, 2-isopropoxycarbonyl-2-propyl, 2-isobutoxycarbonyl-2-propyl, 1-methoxycarbonyl-2-propyl, 1-ethoxycarbonyl-2-propyl, 1-propoxycarbonyl-2-propyl, 1-butoxycarbonyl-2-propyl, 1-isopropoxycarbonyl-2-propyl, 1-isobutoxycarbonyl-2-propyl, 3-methoxycarbonyl-propyl, 3-ethoxycarbonyl-propyl, 3-propoxycarbonyl-propyl, 3-isopropoxycarbonyl-propyl, 3-butoxycarbonyl-propyl and 3-isobutoxycarbonyl-propyl.

Halogen in general represents fluorine, chlorine, bromine or iodine, preferably fluorine, chlorine or bromine. Halogen particularly preferably represents fluorine or chlorine.

Alkylsulphonyl in general represents a straight-chain or branched hydrocarbon radical which has 1 to 12 carbon atoms and is bonded via an $SO_2$ group. Lower alkylsulphonyl with 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylsulphonyl.

Arylsulphonyl in general represents an aromatic radical which has 6 to about 12 carbon atoms and is bonded via an $SO_2$ group. Examples which may be mentioned are: phenylsulphonyl, naphthylsulphonyl and biphenylsulphonyl.

Preferred compounds of the general formula (I) are those in which $R^1$ represents a thiazolamino radical of the formula

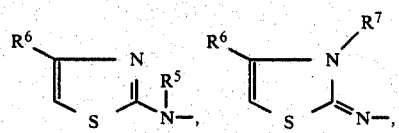, 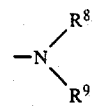

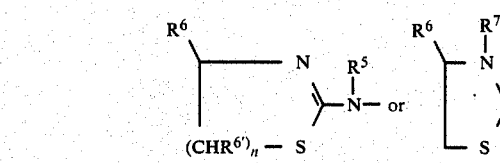

wherein $R^5$ represents hydrogen, lower alkyl, benzyl, benzoyl or acetyl, $R^6$ and $R^{6'}$ are identical or different and represent hydrogen, lower alkyl or phenyl, $R^7$ represents lower alkyl, cyclohexyl, benzyl, acetyl, benzoyl or phenyl and n represents the number 1 or 2, $R^2$ and $R^3$ are identical or different and represent hydrogen, lower alkyl, lower alkenyl, lower alkoxy, lower alkylthio, halogeno-lower alkyl, halogeno-lower alkoxy, trifluoromethylthio, phenyl, benzyl, phenoxy, benzyloxy, lower alkylcarbonyl, benzoyl, carboxyl, lower alkoxycarbonyl, carboxy-lower alkyl, lower alkoxycarbonyl-lower alkyl, nitro, cyano, fluorine, chlorine or bromine, or represent the group of the formula

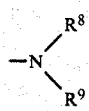

wherein $R^8$ and $R^9$ are identical or different and represent hydrogen, lower alkyl, phenyl, benzyl, lower alkylcarbonyl, benzoyl, trifluoroacetyl, lower alkylsulphonyl, phenylsulphonyl, trifluoromethylphenylsulphonyl or tolylsulphonyl, and $R^4$ has one of the abovementioned meanings of $R^1$, or represents hydrogen, lower alkyl, lower alkenyl, lower alkoxy, lower alkylthio, halogeno-lower alkyl, halogeno-lower alkoxy, trifluoromethylthio, phenyl, benzyl, phenoxy, benzyloxy, lower alkylcarbonyl, benzoyl, carboxyl, lower alkoxycarbonyl, carboxy-lower alkyl, lower alkoxy-lower alkyl, nitro, cyano, fluorine, chlorine or bromine, or represents a group of the formula

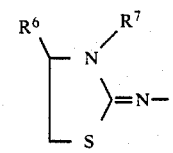

wherein $R^8$ and $R^9$ have the abovementioned meaning, and salts thereof.

Particularly preferred compounds of the formula (I) are those in which $R^1$ represents a thiazolamino radical of the formula

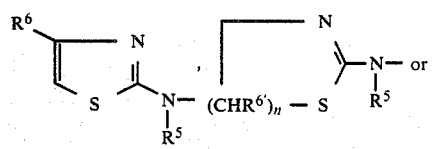

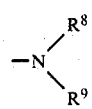

wherein $R^5$ represents hydrogen, methyl, ethyl, propyl, isopropyl, benzyl or acetyl, $R^6$ and $R^{6'}$ are identical or different and represent hydrogen, methyl, ethyl, propyl, isopropyl, butyl, isobutyl or phenyl and $R^7$ represents methyl, ethyl or acetyl, $R^2$ and $R^3$ are identical or different and represent hydrogen, methyl, ethyl, propyl, isopropyl, allyl, methoxy, methylthio, trifluoromethyl, trifluoromethoxy, difluoromethoxy, trifluoromethylthio, acetyl, carboxyl, carboxymethyl, methoxycarbonyl, ethoxycarbonyl, methoxycarbonylmethyl, 1-methoxycarbonyl-ethyl, 2-methoxycarbonyl-ethyl, 2-ethoxycarbonyl-methyl, 1-ethoxycarbonyl-ethyl, 2-ethoxycarbonyl-ethyl, cyano, fluorine, chlorine or bromine, $R^4$ has one of the abovementioned meanings of $R^1$, or represents hydrogen, methyl, ethyl, propyl, isopropyl, butyl, tert.-butyl, methoxy, methylthio, trifluoromethyl, trifluoromethoxy, trifluoromethylthio, acetyl, carboxyl, methoxycarbonyl, ethoxycarbonyl, carboxymethyl, methoxycarbonyl-methyl, ethoxycarbonyl-methyl, 1-methoxycarbonyl-ethyl, 2-methoxycarbonyl-ethyl, 1-ethoxycarbonyl-ethyl, 2-ethoxycarbonyl-ethyl, nitro, cyano, fluorine, chlorine, bromine or a group of the formula

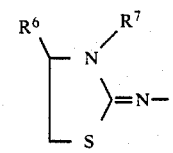

wherein $R^8$ and $R^9$ are identical or different and represent hydrogen, methyl, ethyl, propyl, isopropyl, phenyl, benzyl, acetyl, trifluoroacetyl, methylsulphonyl, phenylsulphonyl, trifluoromethylphenylsulphonyl or tolylsulphonyl,
and salts thereof.

The diaryl sulphide derivatives according to the invention can also be in the form of their salts. Salts of the substances according to the invention with organic and inorganic acids may be mentioned in general here.

Physiologically acceptable salts are preferred in the context of the present invention. Physiologically acceptable salts of the diaryl sulphide derivatives can be salts with inorganic or organic acids. Salts with mineral acids, such as, for example, hydrochlorides, hydrobromides, hydrogen sulphates, sulphates, hydrogen phosphates or phosphates, or with organic carboxylic acids, such as lactic acid, maleic acid, fumaric acid, acetic acid, tartaric acid, citric acid, malic acid or benzoic acid, are preferred.

The following diaryl sulphide derivatives may be mentioned as examples: bis-[4-($\Delta^2$-thiazolin-2-yl)aminophenyl]sulphide, bis-[4-(4-phenyl-$\Delta^2$-thiazolin-2-yl)aminophenyl]sulphide, [2-phenylthio-5-($\Delta^2$-thiazolin-2-yl)amino]phenylacetic acid, methyl [2-phenylthio-5-($\Delta^2$-thiazolin-2-yl)amino]phenylacetate, bis-[4-(5-methyl-$\Delta^2$-thiazolin-2-yl)aminophenyl]sulphide, bis-[4-(4-methyl-$\Delta^2$-thiazidin-2-yl)aminophenyl]sulphide, 4-($\Delta^2$-thiazolin-2-yl)amino-4'-aminodiphenyl sulphide, 4-($\Delta^2$-thiazolin-2-yl)amino-4'-tosylaminodiphenyl sulphide, 4-(3-methylthiazolidin-2-yl)imino-4'-tosylaminodiphenyl sulphide, 4,4'-(3,3'-diacetylthiazolidin-2-yl)diimino-diphenyl sulphide, 4-(3-methylthiazolidin-2-yl)imino-4'-amino-diphenyl sulphide, 4-($\Delta^2$-thiazolin-2-yl)amino-4'-chloro-diphenyl sulphide hydrochloride, 4-($\Delta^2$-thiazolin-2-yl)amino-4'-methyl-diphenyl sulphide, 4-methyl-4'-(3-methylthiazolidin-2-yl)imino-diphenyl sulphide, 4-($\Delta^2$-thiazolin-2-yl)amino-4'-thiazol-2-yl-amino-diphenyl sulphide, 4-nitro-4'-($\Delta^2$-thiazol-2-yl)amino-diphenyl sulphide, 4-($\Delta^2$-thiazolin-2-yl)amino-4'-(3-trifluoromethylphenyl)-sulphonylamino-diphenyl sulphide and bis-[4-(5-methyl-$\Delta^2$-thiazolin-2-yl)aminophenyl]sulphide.

A process for the preparation of diaryl sulphide derivatives of the formula

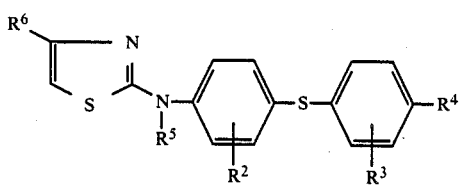

in which
$R^5$ represents hydrogen, alkyl, aralkyl or acyl,
$R^6$ represents hydrogen, alkyl or aryl,
$R^2$ and $R^3$ are identical or different and represent hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represent a group of the formula

wherein
$R^8$ and $R^9$ are identical or different and represent hydrogen, alkyl, aryl, aralkyl, acyl, trifluoroacetyl, alkylsulphonyl, phenylsulphonyl, trifluoromethylphenylsulphonyl or tolylsulphonyl and
$R^4$ represents a radical of the formula

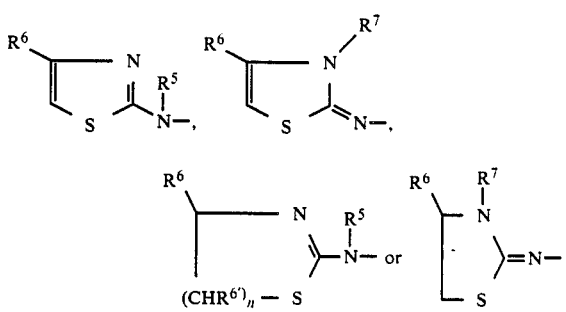

wherein
$R^5$ represents hydrogen, alkyl, aralkyl or acyl,
$R^6$ and $R^{6'}$ are identical or different and represent hydrogen, alkyl, aralkyl or aryl,
$R^7$ represents alkyl, cycloalkyl, aralkyl, aryl or acyl and
n represents the number 1 or 2, or
$R^4$ represents hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkylcarbonyl, carboxyalkyl, alkoxycarbonylalkyl, nitro, cyano or halogen, or represents a group of the formula

wherein
$R^8$ and $R^9$ have the abovementioned meanings, is characterized in that [A] halogen compounds of the general formula (II)

in which
$R^6$ has the abovementioned meaning and
X represents chlorine, bromine or iodine, preferably chlorine or bromine, are reacted with thioureas of the general formula (III)

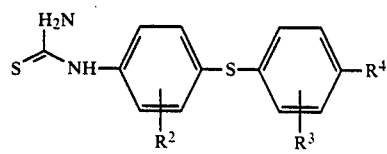

in which
$R^2$, $R^3$ and $R^4$ have the abovementioned meanings, if appropriate in water and/or inert organic solvents, if appropriate in the presence of bases, and, if appropriate, salts obtained are then converted into free compounds with bases, and, if appropriate, these products are alkylated, aralkylated or acylated, or in that [B] thiazoles of the general formula (IV)

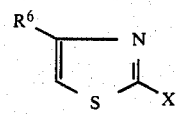 (IV)

in which

X represents chlorine, bromine or iodine, in particular chlorine or bromine, and R$^6$ has the abovementioned meaning, are reacted with amines of the general formula (V)

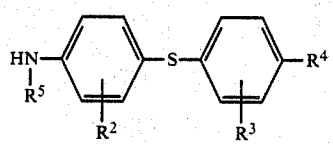 (V)

in which

R$^2$–R$^5$ have the abovementioned meanings, in water and/or inert organic solvents, if appropriate, in the presence of a catalyst, and, if appropriate, salts obtained are converted into the free compounds with bases, or in that [C] thiophenols of the general formula (VI)

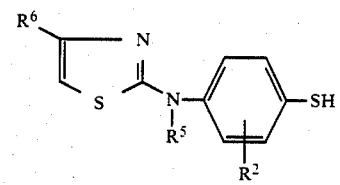 (VI)

in which

R$^2$, R$^5$ and R$^6$ have the abovementioned meanings, are reacted with halogenoaryls of the general formula (VII)

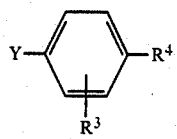 (VII)

in which

R$^3$ and R$^4$ have the abovementioned meanings and

Y represents chlorine, bromine or iodine, preferably iodine or bromine, if appropriate, in water and/or inert organic solvents, in the presence of a base and, if appropriate, in the presence of a catalyst.

Processes A, B and C according to the invention can be illustrated by the following equations:

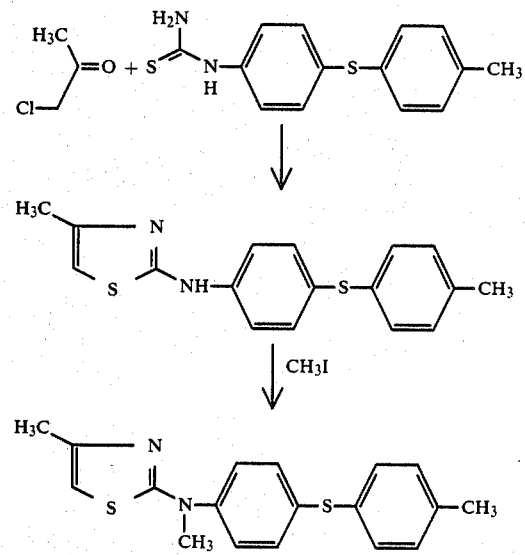 [A]

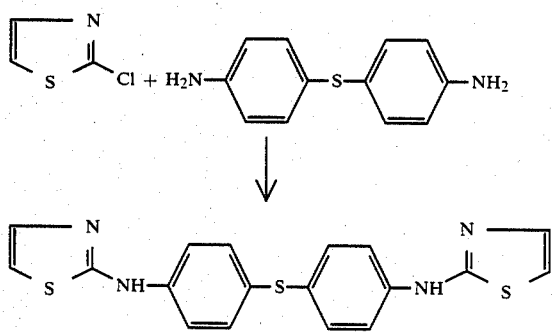 [B]

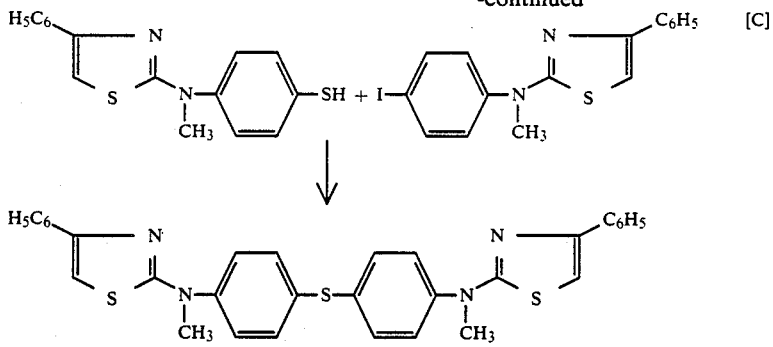

Suitable solvents for processes A, B and C according to the invention are the customary organic solvents which do not change under the reaction conditions. These include, preferably, alcohols, such as, for example, methanol, ethanol, propanol or isopropanol, or ethers, such as, for example, diethyl ether, dioxane, tetrahydrofuran or glycol mono- or dimethyl ether, or hydrocarbons, such as, for example, benzene, toluene, xylene, hexane, cyclohexane, petroleum fractions or decalin, dimethylformamide, hexamethylphosphoric acid triamide, acetonitrile, ethyl acetate or dimethylsulphoxide. It is likewise possible to employ mixtures of the solvents mentioned.

The customary inorganic or organic bases can be employed as bases for the processes according to the invention. These include, preferably, alkali metal hydroxides, such as sodium hydroxide or potassium hydroxide, alkali metal carbonates, such as sodium carbonate, sodium bicarbonate or potassium carbonate, alkali metal alcoholates, such as sodium methanolate or potassium tert.-butanolate, or organic amines, such as triethylamine, pyridine, picoline, N-methylpiperidine, piperidine or morpholine.

Process variants B and C are preferably carried out in the presence of a catalytic amount of copper powder or iron powder, in particular copper powder.

The preparation of the compounds of the formula (Ia) according to the invention by processes A, B and C is in general carried out in a temperature range from 0° C. to 250° C., preferably from 20° C. to 150° C.

The processes according to the invention are in general carried out under normal pressure. However, it is also possible to carry them out under reduced or increased pressure, for example in a range from 0.5 to 5 bar.

In carrying out process A, the thiourea (III) is in general employed in an amount of 0.5 to 5 mol, preferably 1 to 2 mol, per mol of the halogen compound (II). The process according to the invention is carried out, for example, as follows: the halogen compound, the thiourea and a suitable solvent are mixed and, if appropriate, the mixture is warmed. The hydrohalide obtained is converted into the free compound with bases in the customary manner, and, if appropriate, this is then reacted with compounds of the general formula (VIII)

$$R^{5'}-Z \qquad (VIII)$$

in which $R^{5'}$ represents alkyl, aralkyl or acyl and

Z represents halogen, preferably chlorine, bromine or iodine, if appropriate, in the presence of a base, such as, for example, alkali metal hydroxides or alcoholates or organic amines, for example triethylamine, in suitable solvents, such as alcohols, dimethylformamide or dimethylsulphoxide.

In carrying out process B according to the invention, the amine of the formula V is in general employed in an amount of 0.1 to 5 mol, preferably 0.5 to 3 mol, per mol of the thiazole IV. If appropriate, the reaction can be carried out with the addition of a further base in an amount of 1 to 10 mol, preferably 1 to 5 mol, per mol of the thiazole employed. The process according to the invention is carried out, for example, by mixing the amine V, thiazole IV and, if appropriate, the base and catalyst with a suitable solvent and, if appropriate, heating the components or, if appropriate, heating the components under pressure (for example in a closed bomb tube).

In carrying out process C according to the invention, the thiophenol (VI) is in general employed in an amount of 1 to 3 mol, preferably 1 to 1.5 mol, per mol of the halogenoaryl (VII). The base is in general employed in an amount of 1 to 5 mol, preferably 1 to 3 mol, per mol of thiophenol.

The process can be carried out, for example, by preparing the thiophenolate from the thiophenol and a base in an inert solvent and reacting this with halogenoaryls, if appropriate, in suitable solvents, in the presence of catalytic amounts of copper powder. It is also possible here to isolate the thiophenolate.

The halogen compounds of the formula (II) used as starting substances are known or can be prepared by known methods (*Beilstein's Handbuch der organischen Chemie* (Beilstein's Handbook of Organic Chemistry), 7, 283; 1 653; (1), 151).

The thioureas of the formula (III) used as starting substances are known or can be prepared by known methods (Houben-Weyl's "Methoden der organischen Chemie" ("Methods of Organic Chemistry"), IX, 890; IX, 887; *Ullmanns Encyclopadie der Technischen Chemie* (Ullmann's Encyclopaedia of Industrial Chemistry), XIV, 687; and B. Loev et al., *J. Med. Chem.*, 15, 1024 (1972)).

The thiazoles of the formula (IV) employed as starting substances are known or can be prepared by known methods (*Chemistry of Heterocyclic Compounds*, 34/1; and P. Schatzmann, *Liebigs Ann. Chem.*, 261, 10 (1891)).

The amines of the general formula (V) employed as starting compounds are known or can be prepared by known methods, for example by reduction of the corresponding nitro compounds (Houben-Weyl's "Methoden der organischen Chemie" ("Methods of Organic Chemistry"), XI/1, 363).

The thiophenols of the general formula (VI) employed as starting compounds are known or can be prepared by known methods (Houben-Weyl's "Methoden der organischen Chemie" ("Methods of Organic Chemistry"), IX, 12, 26, 818; X/4, 135).

The halogenoaryls of the formula (VII) employed as starting substances are known or can be prepared by known methods (Houben-Weyl's "Methoden der organischen Chemie", ("Methods of Organic Chemistry") V/3, 503, V/4, 517).

A process for the preparation of diaryl sulphide derivatives of the formula

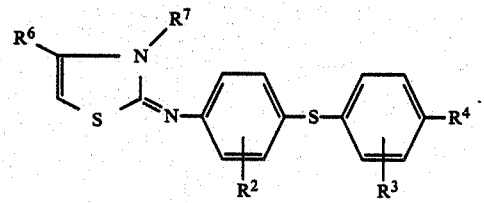
(Ib)

in which
$R^6$ represents hydrogen, alkyl, aralkyl or aryl,
$R^7$ represents alkyl, cycloalkyl, aralkyl, aryl or acyl,
$R^2$ and $R^3$ are identical or different and represent hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represent a group of the formula

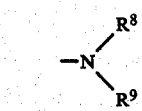

wherein
$R^8$ and $R^9$ are identical or different and represent hydrogen, alkyl, aryl, aralkyl, acyl, trifluoroacetyl, alkylsulphonyl, phenylsulphonyl, trifluoromethylphenylsulphonyl or tolylsulphonyl and
$R^4$ represents a radical of the formula

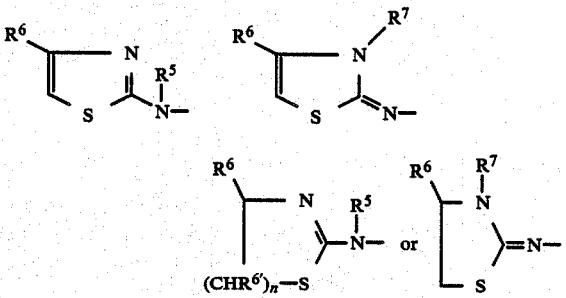

wherein
$R^5$ represents hydrogen, alkyl, aralkyl or aryl,
$R^6$ and $R^{6'}$ are identical or different and represent hydrogen, alkyl or aryl,
$R^7$ represents alkyl, cycloalkyl, aralkyl, aryl or acyl and
n represents the number 1 or 2, or
$R^4$ represents hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkylcarbonyl, carboxylalkyl, alkoxycarbonylalkyl, nitro, cyano or halogen, or represents a group of the formula

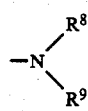

wherein
$R^8$ and $R^9$ have the abovementioned meanings, is characterized in that [D] halogen compounds of the general formula (II) are reacted with substituted thioureas of the general formula (IX)

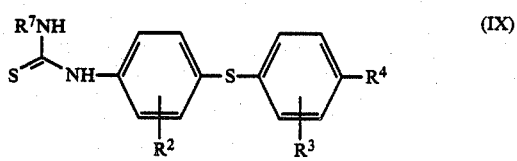
(IX)

in which
$R^2$, $R^3$, $R^4$ and $R^7$ have the abovementioned meanings, if appropriate, in water and/or inert organic solvents, if appropriate, in the presence of a base, and, if appropriate, salts obtained are converted into the free compound with bases.

The preparation of the compounds Ib can be illustrated by the following equation:

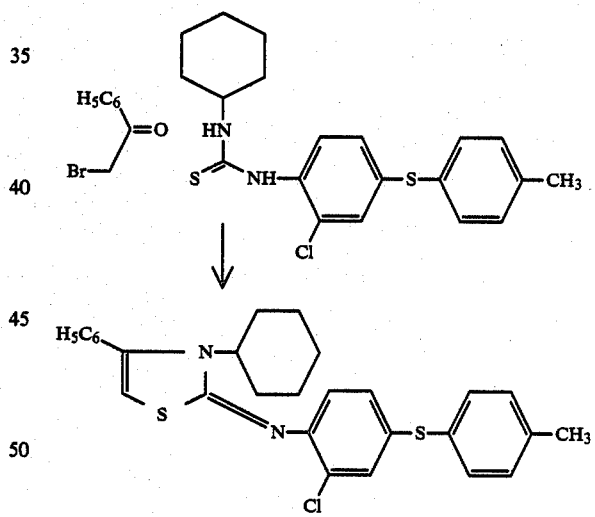

Suitable solvents are water or the customary inert organic solvents which do not change under the reaction conditions. These include, preferably, alcohols, such as methanol, ethanol, propanol or isopropanol, or ethers, such as diethyl ether, dioxane, tetrahydrofuran or glycol mono- or dimethyl ether, hydrocarbons, such as benzene, xylene, toluene or petroleum fractions, or dimethylformamide, dimethylsulphoxide, hexamethylphosphoric acid triamide, acetonitrile or ethyl acetate. It is also possible to employ mixtures of the solvents mentioned.

The reaction is in general carried out in a temperature range from 20° C. to 200° C., preferably from 20° C. to 150° C.

The reaction is in general carried out under normal pressure. However, it is likewise possible to carry out the reaction under increased or reduced pressure (for example, 0.5–5 bar).

In carrying out the process according to the invention, the substituted thiourea IX is in general employed in an amount of 0.1 to 5, preferably 0.5 to 2, mol per mol of the halogen compound II. The process according to the invention is carried out, for example, as follows: the halogen compound and the substituted thiourea are mixed, if appropriate, the mixture is dissolved in a suitable solvent, and, if appropriate, the components are warmed. The hydrohalide obtained is converted into the free compounds with a base in the customary manner. Suitable bases here are the customary inorganic or organic bases. These include, preferably, alkali metal hydroxides, such as sodium hydroxide or potasssium hydroxide, alkali metal carbonates, such as sodium carbonate or potassium carbonate, sodium bicarbonate, alkali metal alcoholates, such as sodium methanolate or ethanolate or potassium methanolate or ethanolate, or triethylamine.

The substituted thioureas employed as starting compounds are known or can be prepared by known methods (Houben-Weyl's "Methoden der organischen Chemie" ("Methods of Organic Chemistry"), IX, 890; and *Org. Synth., Coll.*, Vol. III, 617 (1955)).

A process for the preparation of diaryl sulphide derivatives of the formula

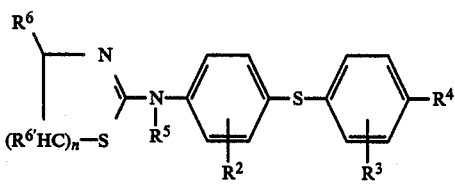
(Ic)

in which $R^5$ represents hydrogen, alkyl or acyl, $R^6$ and $R^{6'}$ are identical or different and represent hydrogen, alkyl or aryl and n represents the number 1 or 2, $R^2$ and $R^3$ are identical or different and represent hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represent a group of the formula

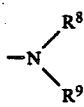

wherein $R^8$ and $R^9$ are identical or different and represent hydrogen, alkyl, aryl, aralkyl, acyl, trifluoroacetyl, alkylsulphonyl, phenylsulphonyl, trifluoromethylphenylsulphonyl or tolylsulphonyl and $R^4$ represents a radical of the formula

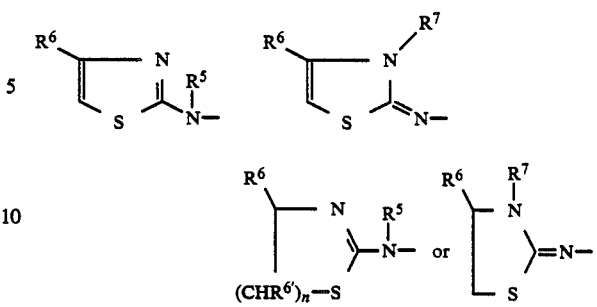

wherein $R^5$ represents hydrogen, alkyl, aralkyl or acyl, $R^6$ and $R^{6'}$ are identical or different and represent hydrogen, alkyl, aralkyl or aryl, $R^7$ represents alkyl, cycloalkyl, aralkyl, aryl or acyl and n represents the number 1 or 2, or $R^1$ represents hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkylcarbonyl, carboxyalkyl, alkoxycarbonylalkyl, nitro, cyano or halogen, or represents a group of the formula

wherein $R^8$ and $R^9$ have the abovementioned meanings, is characterized in that [E] aminoethanols of the general formula (X)

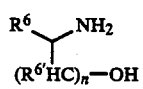
(X)

in which $R^6$, $R^{6'}$ and n have the abovementioned meanings, are reacted with isothiocyanates of the general formula (XI)

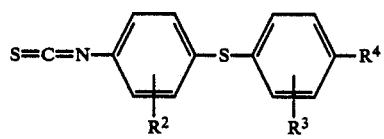
(XI)

in which $R^2$, $R^3$ and $R^4$ have the abovementioned meanings, in inert organic solvents, and, if appropriate, the products are arylated, alkylated or acylated, or in that [F] halogenoisothiocyanates of the general formula XII

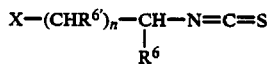
(XII)

in which $R^6$, $R^{6'}$ and n have the abovementioned meanings and

X represents chlorine, bromine or iodine, preferably chlorine or bromine,
are reacted with amines of the general formula (V)

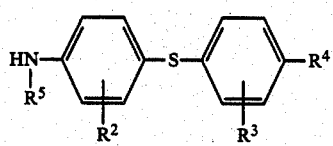  (V)

in which

R², R³, R⁴ and R⁵ have the abovementioned meanings, if appropriate, in the presence of bases in inert organic solvents, or in that [G] thiophenols of the general formula XIII

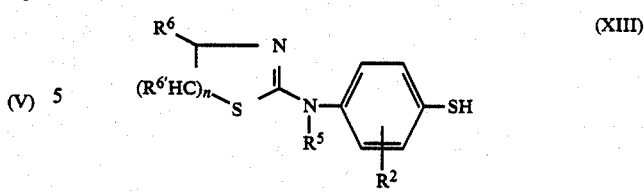 (XIII)

in which

R², R⁵, R⁶, R⁶' and n have the abovementioned meanings,
are reacted with halogenoaryls of the general formula (VII), if appropriate, in water and/or inert organic solvents, in the presence of a base, and, if appropriate, in the presence of a catalyst.

Processes E, F and G according to the invention can be illustrated by the following equations:

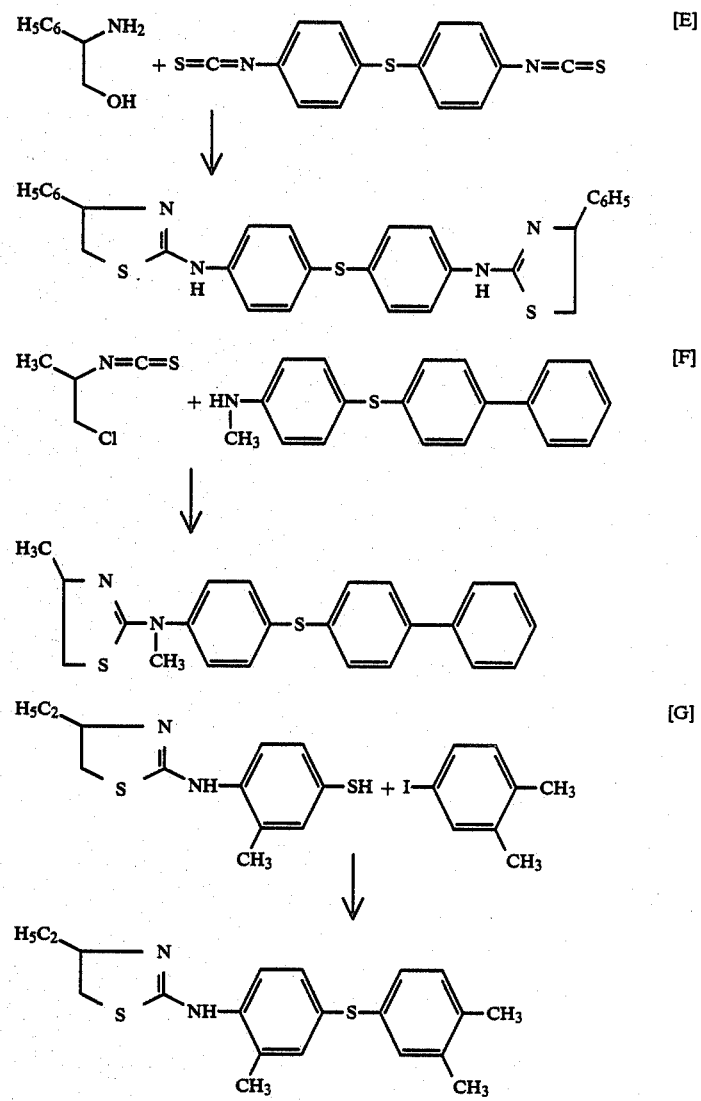

Suitable solvents for processes E and F according to the invention are the customary organic solvents which do not change under the reaction conditions. These include, preferably, ethers, such as diethyl ether, dioxane, tetrahydrofuran or glycol mono- or dimethyl ether, or halogenohydrocarbons, such as methylene chloride, chloroform or carbon tetrachloride, or hydrocarbons, such as benzene, toluene, xylene, hexane, cyclohexane or petroleum fractions. It is also possible to employ mixtures of the solvents mentioned.

Suitable bases in process F are the customary inorganic or organic bases. These include, preferably, trialkylamines, such as triethylamine, or pyridine, picoline, morpholine or N-methylpiperidine, or alkali metal hydroxides, such as sodium or potassium hydroxide, or alkali metal carbonates, such as sodium or potassium carbonate, or sodium bicarbonate.

The reactions in processes E and F are in general carried out in a temperature range from $-10°$ C. to $+150°$ C., preferably from $0°$ C. to $+80°$ C.

Processes E and F according to the invention are in general carried out under normal pressure. However, it is also possible for them to be carried out under increased or reduced pressure (for example, from 0.5 to 5 bar).

In carrying out process E, the aminoethanol (X) is in general employed in an amount of 1 to 10, preferably 1 to 5, mol per mol of isothiocyanate (XI), and in process F in general 0.5 to 10, preferably 1 to 5, mol of halogenoisothiocyanate XII and 0.5 to 10 mol, preferably 1 to 5 mol, of base are employed per mole of amine (V).

Processes E and F are carried out, for example, by mixing the components with a suitable solvent and, if appropriate, heating the mixture. Working up is carried out in the generally known manner and is familiar to the expert.

The procedure and the conditions for process G are analogous to those which have already been described for process C.

The aminoalcohols of the formula X employed as starting substances are known or can be prepared by known methods (*Beilstein's Handbuch der organischen Chemie* (Beilstein's Handbook of Organic Chemistry), XII, 182; IV, 275).

The isothiocyanates of the formula XI employed as starting substances are known or can be prepared by known methods (Houben-Weyl's "Methoden der organischen Chemie" ("Methods of Organic Chemistry"), IX, 875).

The halogenoisothiocyanates XII employed as starting substances are known or can be prepared by known methods (R. E. Hackler, T. W. Balko, *Synth. Commun.*, 5, 43 (1975)).

The thiophenols of the formula XIII employed as starting substances are known or can be prepared by known methods (for example Houben-Weyl's "Methoden der organischen Chemie" ("Methods of Organic Chemistry"), IX, 12, 16, 818; X/4, 135).

A process for the preparation of diaryl sulphide derivatives of the formula

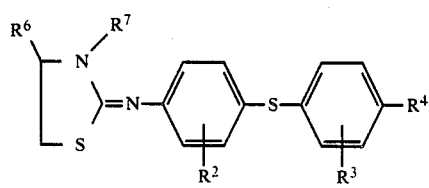
(Id)

in which
$R^6$ represents hydrogen, alkyl or aryl and
$R^7$ represents alkyl, cycloalkyl, aralkyl, aryl or acyl, $R^2$ and $R^3$ are identical or different and represent hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represent a group of the formula

wherein
$R^8$ and $R^9$ are identical or different and represent hydrogen, alkyl, aryl, aralkyl, acyl, trifluoroacetyl, alkylsulphonyl, phenylsulphonyl, trifluoromethylphenylsulphonyl or tolylsulphonyl and
$R^4$ represents a radical of the formula

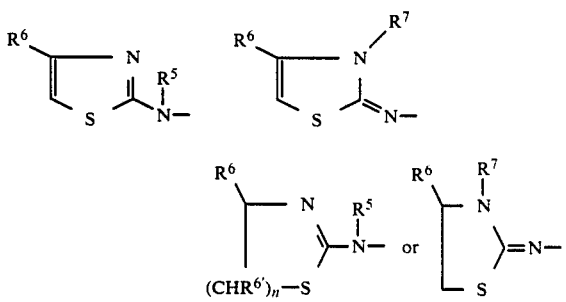

wherein
$R^5$ represents hydrogen, alkyl, aralkyl or acyl,
$R^6$ and $R^{6'}$ are identical or different and represent hydrogen, alkyl, aralkyl or aryl,
$R^7$ represents alkyl, cycloalkyl, aralkyl, aryl or acyl and
n represents the number 1 or 2, or
$R^4$ represents hydrogen, alkyl, alkenyl, cycloalkyl, alkoxy, alkylthio, halogenoalkyl, halogenoalkoxy, halogenoalkylthio, aryl, aralkyl, aryloxy, aralkoxy, aralkylthio, acyl, carboxyl, alkoxycarbonyl, carboxyalkyl, alkoxycarbonylalkyl, nitro, cyano or halogen, or represents a group of the formula

wherein
$R^8$ and $R^9$ have the abovementioned meanings, is characterized in that [H] dihalogeno compounds of the general formula (XIV)

(XIV)

in which
$R^6$ has the meaning given and
X represents chlorine, bromine or iodine, preferably chlorine or bromine, are reacted with substituted thioureas of the general formula (IX)

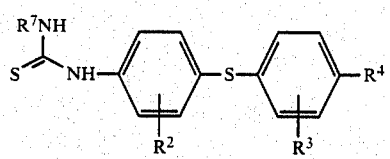

(IX)

in which

R², R³, R⁴ and R⁷ have the abovementioned meanings, if appropriate, in water and/or inert organic solvents, if appropriate, in the presence of bases, and, if appropriate, salts obtained are converted into the free compounds with bases.

The preparation of the compounds of the formula Id according to the invention can be illustrated by the following equation:

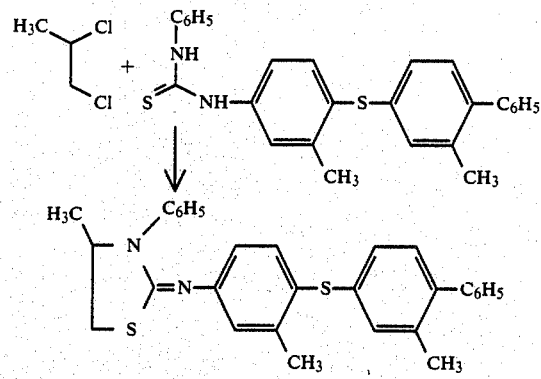

Suitable solvents are water or the customary inert organic solvents which do not change under the reaction conditions. These include, preferably, alcohols, such as methanol, ethanol, propanol or isopropanol, or ethers, such as diethyl ether, dioxane, tetrahydrofuran or glycol mono- or dimethyl ether, hydrocarbons, such as benzene, xylene, toluene or petroleum fractions, or dimethylformamide, dimethylsulphoxide, hexamethylphosphoric acid triamide, acetonitrile or ethyl acetate. It is also possible to employ mixtures of the solvents mentioned.

The reaction is in general carried out in a temperature range from 20° C. to 200° C., preferably from 20° C. to 150° C.

The reaction is in general carried out under normal pressure. However, it is also possible for it to be carried out under increased or reduced pressure (for example 0.5–5 bar).

In carrying out the process according to the invention, the substituted thiourea IX is in general employed in an amount of 0.1 to 5, preferably 0.5 to 2 mol per mol of the halogen compound XIV. The process according to the invention is carried out, for example, as follows: the halogen compound and the substituted thiourea are mixed, if appropriate, the mixture is dissolved in a suitable solvent and if appropriate the components are warmed. The hydrohalide obtained is converted into the free compounds with bases in the customary manner. Suitable bases here are the customary inorganic or organic bases. These include, preferably, alkali metal hydroxides, such as sodium or potassium hydroxide, alkali metal carbonates, such as sodium or potassium carbonate, sodium bicarbonate, alkali metal alcoholates, such as sodium methanolate or ethanolate or potassium methanolate or ethanolate, or triethylamine.

The substituted thioureas employed as starting compounds are known or can be prepared by known methods (Houben-Weyl's "Methoden der organischen Chemie" ("Methods of Organic Chemistry"), IX, 890; and Org. Synth., Coll. Vol. III, 617 (1955)).

The diaryl sulphides of the formula (I) according to the invention can be employed as active compounds in medicaments for human medicine and/or veterinary medicine. Surprisingly, the substances act as inhibitors (stimulators) of enzymatic reactions in the context of arachidonic acid metabolism, in particular of lipoxygenase.

They are thus preferably suitable for the treatment and prevention of diseases of the respiratory tract, such as allergies, asthma, bronchitis, emphysema, shock lung; cardiovascular diseases; inflammations; rheumatism; psoriasis; oedemas; thromboses; thromboembolisms and ischaemias (disturbances in peripheral, cardiac and cerebral circulation), during tissue transplants and for cytoprotection in the gastrointestinal tract.

The new active compounds can be converted in a known manner into the customary formulations, such as tablets, capsules, dragees, pills, granules, aerosols, caplets, syrups, emulsions, suspensions and solutions, using inert non-toxic pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate, using emulsifying agents and/or dispersing agents, and, for example, in the case of the use of water as the diluent, organic solvents can be used as auxiliary solvents, if appropriate.

Examples of auxiliaries which may be mentioned are: water, non-toxic organic solvents, such as paraffins (for example, petroleum fractions), vegetable oils (for example, groundnut/sesame oil), alcohols (for example, ethyl alcohol and glycerol) and glycols (for example, propylene glycol and polyethylene glycol), solid excipients, such as, for example, natural rock powders (for example, kaolins, aluminas, talc and chalk), synthetic rock powders (for example highly disperse silicic acid and silicates), sugars (for example, sucrose, lactose and glucose), emulsifying agents (for example, polyoxyethylene fatty acid esters, polyoxyethylene fatty alcohol ethers (alkyl sulphonates and aryl sulphonates), dispersing agents (for example, lignin sulphite waste liquors, methylcellulose, starch and polyvinylpyrrolidone) and lubricants (for example, magnesium stearate, talc, stearic acid and sodium sulphate).

Administration is effected in the customary manner, preferably orally or parenterally, in particular perlingually or intravenously. In the case of oral use, tablets can of course also contain additives, such as sodium citrate, calcium carbonate and dicalcium phosphate, together with various adjuvants, such as starch, preferably potato starch, gelatine and the like, in addition to the excipients mentioned. Lubricants, such as magnesium stearate, sodium lauryl-sulphate and talc, can furthermore be co-used for tablet-making. In the case of aqueous suspensions and/or elixirs intended for oral use, various flavour-improving agents or dyestuffs can be added to the active compounds, in addition to the abovementioned auxiliaries.

In the case of parenteral use, solutions of the active compounds can be employed, using suitable liquid excipients.

In general, it has proved advantageous, in the case of intravenous administration, to administer amounts of about 0.001 to 1 mg/kg, preferably about 0.01 to 0.5 mg/kg of body weight, in order to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular to do so as a function of the body weight or of the mode of administration, but also as a function of the individual behaviour towards the medicament or the nature of its formulation and the period or interval at which administration takes place. Thus, in some cases it may suffice to manage with less than the abovementioned minimum amount, whilst in other cases the upper limit mentioned must be exceeded. Where relatively large amounts are administered, it may be advisable to divide these into several individual doses over the course of the day.

PREPARATION EXAMPLES

Example 1

Bis(4-isothiocyanatophenyl)sulphide

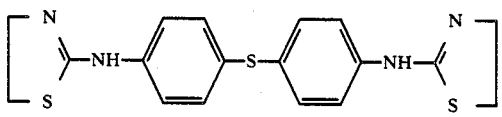

A filtered solution of 47.5 g of bis(4-aminophenyl)sulphide in 1.5 l of toluene is slowly added dropwise to a solution of 31 ml of thiophosgene in 300 ml of toluene, while cooling with ice. The mixture is stirred at 0° C. for 30 minutes and warmed to 10° C. and a solution of 110 ml of triethylamine in 150 ml of toluene is added dropwise. The mixture is subsequently stirred at 15° C. for a further 30 minutes and at room temperature for 2 hours, the precipitate is then filtered off with suction and the solution is concentrated in vacuo at 40° C. The residue is chromatographed on silica gel with cyclohexane.

Melting point: 78°–79° C.
Yield: 64% of theory

Example 2

Bis[4-($\Delta^2$-thiazolin-2-yl)aminophenyl]sulphide

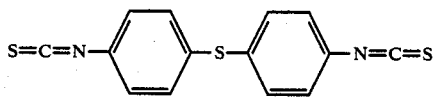

12.2 ml of aminoethanol are slowly added dropwise to a mixture of 30.4 g of bis(4-isothiocyanatophenyl)sulphide and 250 ml of ethanol at 0° C.–5° C. and the mixture is stirred at 0° C. for 2 hours. The precipitate is filtered off with suction. For purification, the residue is dissolved with concentrated hydrochloric acid at the boiling point and the solution is stirred overnight at room temperature. The pH is brought to 9 with 45% strength sodium hydroxide solution, while cooling with ice, and the precipitate is filtered off with suction, washed with water and dried.

Melting point: 195°–195.5° C.
Yield: 81% of theory.

Example 3

Bis[4-($\Delta^2$-thiazolin-2-yl)aminophenyl]sulphide HCl salt

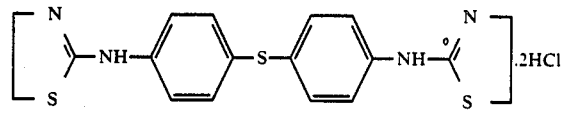

3 g of bis[4-($\Delta^2$-thiazolin-2-yl)aminophenyl]sulphide are taken up in 0.6 ml of 1N HCl and 10 ml of H$_2$O and the mixture is lyophilized.

Yield: quantitative
Hygroscopic crystals which deliquesce in air

Example 4

Bis[4-(4-phenyl-$\Delta^2$-thiazolin-2-yl)aminophenyl]sulphide

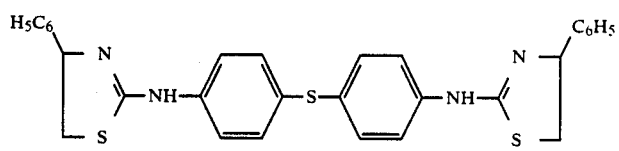

5.6 g of bis(4-isothiocyanatophenyl)sulphide and 5.5 g of 2-amino-2-phenylethanol are dissolved in 100 ml of methylene chloride and the solution is stirred at 0° C. for 1 hour. The precipitate is filtered off with suction and dissolved in concentrated HCl at the boiling point. After cooling, the pH is brought to 7 with sodium hydroxide solution. The precipitate is filtered off with suction, boiled up with ether/hexane=1:1 and chromatographed on silica gel (mobile phase methylene chloride).

Melting point: 70° C., decomposition.
Yield: 68% of theory.

Example 5

(5-Nitro-2-phenylthio)phenylacetic acid

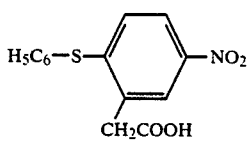

40.5 g of thiophenol are added dropwise to a solution of 39.5 g of KOH in 400 ml of H$_2$O. 71 g of (2-chloro-5-nitro)phenylacetic acid and 4 g of copper powder are then added in portions to the mixture and the mixture is heated under reflux for 7 hours. It is filtered while still hot, cooled and acidified with hydrochloric acid. The aqueous phase is decanted off from the oil which has separated out and the product is crystallized with ethanol/water.
Yield: 53% of theory
Melting point: 135° C.

Example 6

Methyl(5-nitro-2-phenylthio)phenylacetate

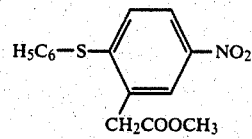

3 g of sulphuric acid are added to 40 g of (5-nitro-2-phenylthio)phenylacetic acid in 200 ml of methanol, the mixture is heated under reflux for 2 hours and cooled and the solution is evaporated. 200 ml of ether and 200 ml of ice-water are added to the residue, the phases are separated and the aqueous phase is extracted 3 times with ether. The combined ether phases are washed twice with saturated sodium carbonate solution, dried over sodium sulphate and concentrated.
Yield: 98% of theory.
Melting point: yellow oil

Example 7

Methyl(5-amino-2-phenylthio)phenylacetate

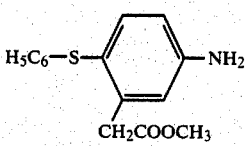

135.5 g of tin-(II) chloride hydrate are introduced in portions into a solution of 40.3 g of methyl(5-nitro-2-phenylthio)phenylacetate and 450 ml of acetic acid, 175 ml of concentrated hydrochloric acid are added and the mixture is heated under reflux for 5 hours. After cooling, the mixture is concentrated and the residue is stirred with 550 ml of 10% strength sodium hydroxide solution, filtered off with suction and dissolved again in 1 l of dilute hydrochloric acid. After the solution has been left to stand overnight, 22.5 g of colorless crystals are obtained.
Yield: 63% of theory.
Melting point: 95° C., decomposition.

Example 8

Methyl(5-isothiocyanato-2-phenylthio)phenylacetate

22 g of methyl(5-amino-2-phenylthio)phenylacetate in 500 ml of toluene are added to a solution of 9.2 g of thiophosgene in 200 ml of toluene at 0° C. and the mixture is stirred in an ice-bath for 4 hours. After concentration, the residue is chromatographed on silica gel with methylene chloride.
Yield: 32% of theory.

Melting point: 81°-82° C.

Example 9

[2-Phenylthio-5-($\Delta^2$-thiazolin-2-yl)amino]phenylacetic acid

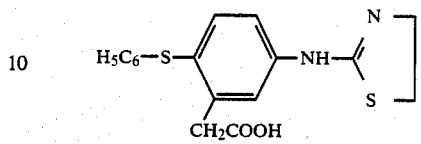

1.8 g of aminoethanol are added dropwise to 8 g of methyl(5-isothiocyanato-2-phenylthio)phenylacetate in 150 ml of methylene chloride at 0° C. After the mixture has been stirred for 30 minutes, it is evaporated, the precipitate is suspended in concentrated hydrochloric acid and the suspension is heated at the boiling point for 1 hour. A clear solution thereby forms, from which 6.9 g of acid precipitate on cooling.
Yield: 79% of theory
Melting point: 159°-60° C.

Example 10

Methyl[2-phenylthio-5-($\Delta^2$-thiazolin-2-yl)amino]phenylacetate

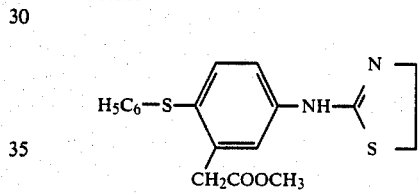

5.3 g of product are obtained analogously to Example 5 from [2-phenylthio-5-($\Delta^2$-thiazolin-2-yl)amino]phenylacetic acid and methanol.
Yield: 74% of theory
Melting point: 122°-4° C.

Example 11

4-(Phenylthio)phenyl isothiocyanate

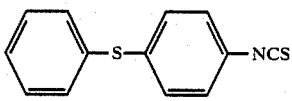

A solution of 20.1 g of 4-phenylthioaniline in 250 ml of toluene and then 20.2 g of triethylamine are added dropwise in succession to a solution of 11.9 g of thiophosgene in 250 ml of toluene, while cooling with ice, and the mixture is stirred for 1 hour. After warming to room temperature, it is filtered with suction over kieselguhr and the filtrate is evaporated. Hexane is added to the oil which remains, the mixture is filtered and the filtrate is evaporated again. Chromatography of the residue on silica gel with cyclohexane gives a clear oil.
Yield: 82% of theory.

Example 12

2-[N-(4-Phenylthio)phenyl]amino-$\Delta^2$-thiazoline

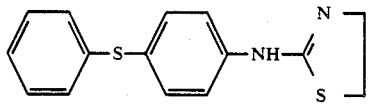

5 g of aminoethanol are added dropwise to a solution of 20 g of (4-phenylthio)phenyl isothiocyanate in 250 ml of methylene chloride, while cooling with ice, and the mixture is stirred for 1 hour. Thereafter, the mixture is heated under reflux for a further hour, cooled and filtered with suction and the residue is rinsed with water. The residue is dissolved in methylene chloride and the organic phase is washed with sodium hydroxide solution, dried and evaporated.

Yield: 79% of theory.
Melting point: 99° C.

Example 13

4-(4-Cyanophenylthio)phenyl isothiocyanate

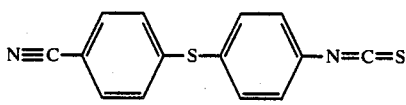

A solution of 4.3 g of 4-(4-(4-cyanophenylthio)aniline in 100 ml of toluene and then 3.8 g of triethylamine are added dropwise in succession to a solution of 2.3 g of thiophosgene in 50 ml of toluene, while cooling with ice, and the mixture is stirred for 1 hour, while cooling with ice, and then for 1 hour at room temperature. The mixture is filtered with suction over kieselguhr, the filtrate is evaporated on a rotary evaporator and the residue is chromatographed on silica gel with cyclohexane.

Yield: 83% of theory.
Melting point: 91° C.

Examples 14, 15 and 16

2-[4-(4-Cyanophenylthio)phenyl]amino-Δ²-thiazoline 14

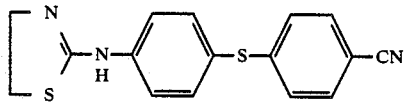

4-[4-(Δ²-Thiazolin-2-yl)aminophenylthio]benzoic acid 15

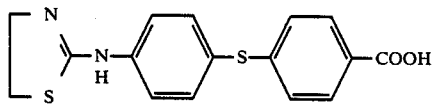

and
4-[4-(Δ²-Thiazolin-2-yl)aminophenylthio]benzoic acid amide 16

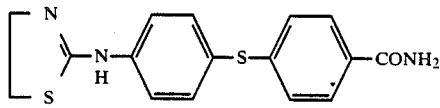

9 g of aminoethanol are added dropwise to a solution of 4 g of 4-(4-cyanophenylthio)phenyl isothiocyanate in 100 ml of methylene chloride, while cooling with ice, and the mixture is stirred for 1 hour and filtered with suction. The residue is dissolved in 100 ml of concentrated HCl and the solution is heated under reflux for 1 hour. After cooling, NaOH is added until the mixture is alkaline, and the precipitate formed is filtered off with suction.

Yield: 0.1 g of 14
Melting point: 135°-6° C.

The mother liquor is acidified with HCl, methylene chloride is added and the precipitate formed between the phases is filtered off with suction.

Yield: 0.5 g of 15
Melting point: 210°-2° C.

The two phases are then separated and the aqueous phase is extracted twice with methylene chloride. The organic phase is dried over $Na_2SO_4$ and evaporated.

Yield: 0.1 g of 16
Melting point: 192°-3° C.

Example 17

Bis[4-(3-methyl-thiazolidin-2-imino)phenyl]sulphide

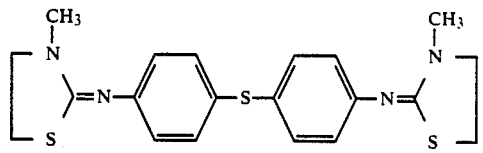

Process variant A:

4.8 g of bis[4-(Δ²-thiazolin-2-yl)aminophenyl]sulphide are dissolved in 100 ml of dried dimethylformamide and 0.75 g of sodium hydride is added. The mixture is allowed to react in an ultrasonic bath at room temperature for 2 hours and is cooled to 0° to 5° C. and 1.6 ml of methyl iodide are added. The mixture is stirred in an ice-bath for 1 hour and at room temperature for a further hour and is then concentrated to dryness in vacuo. The residue is suspended in methylene chloride and the suspension is washed with 2N hydrochloric acid. The aqueous phase is rendered alkaline with 2N sodium hydroxide solution and evaporated to dryness in vacuo and the residue is extracted by stirring in methylene chloride. The insoluble material is then filtered off, the filtrate is concentrated to dryness in vacuo and the oil which remains is chromatographed over silica gel with methylene chloride/methanol=9/1.

Yield: 4% of theory
Melting point: 130°-140° C.

Process variant B:

0.9 g of bis(4-isothiocyanatophenyl)sulphide is dissolved in 20 ml of methylene chloride, the solution is cooled to 0° to 5° C. and 0.2 g of N-methylethanolamine is added. The mixture is stirred for 1 hour, while cooling with ice, and filtered with suction. The residue is dissolved in 20 ml of concentrated hydrochloric acid and the solution is heated under reflux for 1 hour, cooled and rendered alkaline with ammonia. The precipitate is filtered off with suction and dried.

Yield: 22% of theory
Melting point: 139°-141° C.

Example 18

4-(4-Trifluoromethylphenylthio)phenyl isothiocyanate

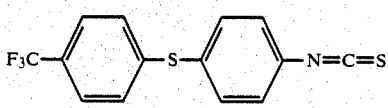

A filtered solution of 4.5 g of 4-(4-trifluoromethylphenyl)thio-aniline in 150 ml of toluene and then 3.4 g of triethylamine are slowly added dropwise to a solution of 2 g of thiophosgene in 50 ml of toluene, while cooling with ice. The mixture is stirred for 2 hours, while cooling with ice, and evaporated on a rotary evaporator and the residue is chromatographed over a silica gel column with cyclohexane.

Yield: 77% of theory.
Melting point: 46°-47° C.

Example 19

2-[N-4-(4-Trifluoromethylphenylthio)phenyl]amino-Δ²-thiazoline hydrochloride

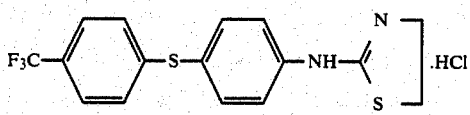

0.8 g of ethanolamine is added dropwise to a solution of 4.1 g of 4-(4-trifluoromethylphenylthio)phenyl isothiocyanate in 50 ml of methylene chloride, while cooling with ice, the mixture is stirred for 30 minutes, while cooling with ice, and the precipitate is filtered off with suction.

The residue is suspended in 100 ml of concentrated hydrochloric acid and the suspension is heated under reflux for 1 hour, cooled and rendered alkaline with ammonia. The residue is filtered off with suction and taken up in hydrochloric acid and the mixture is again rendered alkaline with ammonia. The precipitate is filtered off with suction, stirred in water overnight, filtered off with suction again and dried.

Yield: 74% of theory
Melting point: 78°-80° C.

Example 20

Bis[4-(3-cyclohexyl-5-methyl-thiazolidin-2-imino)-phenyl]sulphide

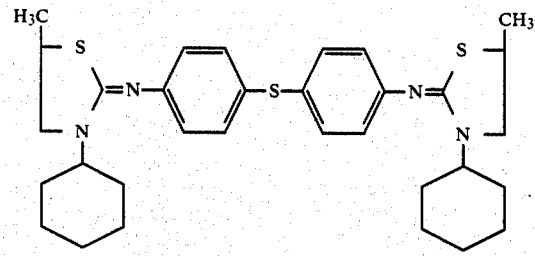

A solution of 5.2 g of N-cyclohexylamino-1-methylethanol in 20 ml of methylene chloride is added dropwise to a mixture of 10 g of bis(4-isothiocyanatophenyl)sulphide in 100 ml of methylene chloride, while cooling with ice, and the mixture is stirred at 0° to 5° C. for 1 hour and filtered with suction. The residue is suspended in 150 ml of concentrated hydrochloric acid and the suspension is heated under reflux for 1 hour. After cooling, the product is precipitated with ammonia, the residue is taken up again in concentrated hydrochloric acid and the mixture is rendered alkaline again with ammonia. The precipitate is filtered off with suction and dried. The residue is chromatographed over a silica gel column with methylene chloride/methanol=50:1.

Yield: 2% of theory.
Melting point: 198° C.

Example 21

2-[4-(4-Aminophenylthio)phenyl]imino-3-phenyl-thiazolidine

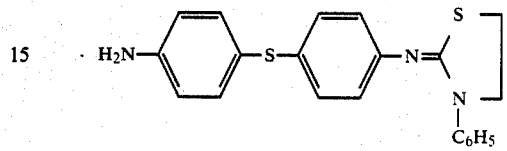

9.2 g of phenylethanolamine are added dropwise to a mixture of 10 g of bis(4-isocyanatophenyl)sulphide in 100 ml of methylene chloride, while cooling with ice, and the mixture is stirred for 1 hour, while cooling with ice. The residue is filtered off with suction and suspended in 100 ml of concentrated hydrochloric acid and the suspension is heated under reflux for 1 hour, cooled, rendered alkaline with ammonia and filtered with suction again. The residue is dissolved in concentrated hydrochloric acid, the solution is rendered alkaline again with ammonia and the precipitate is filtered off with suction and dried. The residue is chromatographed over silica gel with methylene chloride/methanol=50:1.

Yield: 6% of theory
Melting point: 143°-145° C.

Example 22

Bis[4-(5-methyl-Δ²-thiazolin-2-yl)aminophenyl]sulphide

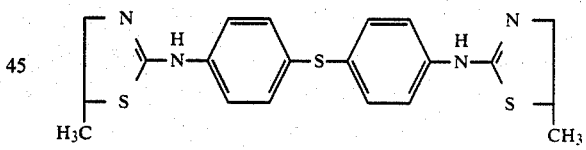

10 g (0.033 mol) of bis(4-isothiocyanatophenyl)sulphide are dissolved in 100 ml of methylene chloride, the solution is cooled to 0°-5° C. and 5.0 g=5.2 ml (0.066 mol) of amino-2-hydroxypropane are added dropwise. The mixture is subsequently stirred at 0°-5° C. for about a further hour and evaporated to dryness in vacuo and the residue is suspended in concentrated hydrochloric acid. The suspension is heated under reflux for 1 hour, a clear solution slowly forming. After cooling, the product is precipitated by careful addition of a concentrated ammonia solution, while stirring; if necessary, reprecipitation with hydrochloric acid/ammonia.

Yield: 1.2 g (8.7% of theory)
Melting point: 192° C. (decomposition)

Example 23

Bis[4-(4-methyl-Δ²-thiazolin-2-yl)aminophenyl]sulphide

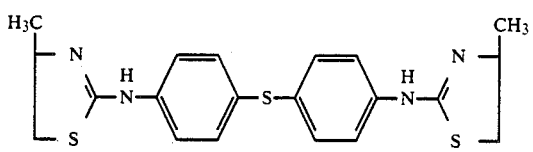

10 g (0.033 mol) of bis(4-isothiocyanatophenyl)sulphide are dissolved in 100 ml of methylene chloride, the solution is cooled to 0°–5° C. and 5.0 g≡5.2 ml (0.066 mol) of 2-amino-1-hydroxypropane are added dropwise. The mixture is subsequently stirred at 0°–5° C. for about a further hour and evaporated to dryness in vacuo and the residue is suspended in concentrated hydrochloric acid. The suspension is heated under reflux for 1 hour, a clear solution slowly forming. After cooling, the product is precipitated by careful addition of a concentrated ammonia solution, while stirring; if necessary, reprecipitation with hydrochloric acid/ammonia.

Yield: 1.6 g (11.7% of theory)
Melting point: 180° C. (decomposition)

Example 24

Bis[4-(5,6-dihydro-1,3-thiazin-2-yl)aminophenyl]sulphide

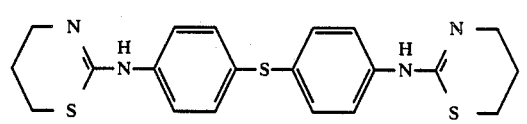

4.2 g (0.014 mol) of bis(4-isothiocyanatophenyl)sulphide are dissolved in 50 ml of methylene chloride, the solution is cooled to 0°–5° C. and 2.1 g≡2.2 ml (0.028 mol) of 1-amino-3-hydroxypropane are added dropwise. The mixture is subsequently stirred at 0°–5° C. for about a further hour and evaporated to dryness in vacuo and the residue is suspended in concentrated hydrochloric acid. The suspension is heated under reflux for 1 hour, a clear solution slowly forming. After cooling, the product is precipitated by careful addition of a concentrated ammonia solution, while stirring; if necessary, reprecipitation with hydrochloric acid/ammonia.

Yield: 5.6 g (96.6% of theory)
Melting point: 172° C. (decomposition)

Example 25

4-Tosylamino-4'-nitrodiphenyl sulphide

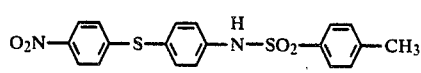

25.1 g (0.1 mol) of 4-amino-4'-nitrodiphenyl sulphide are dissolved in 1,500 ml of dioxane, and 8 ml (0.1 mol) of pyridine are added. 19.4 g (0.1 mol) of tosyl chloride in 200 ml of dioxane are added dropwise to this solution. The temperature thereby drops to 12° C. the mixture is warmed under reflux overnight. After cooling, it is evaporated to dryness in vacuo, the residue is taken up in about 1 l of ethyl acetate and the mixture is washed twice with 2N sodium hydroxide solution. After washing until neutral and drying, the solvent is evaporated off in vacuo and the residue is stirred with diethyl ether.

Yield: 20.5 g (51.3% of theory)
Melting point: 324° C. (decomposition)

Example 26

4-Tosylamino-4'-aminodiphenyl sulphide

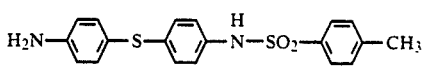

18 g (0.045 mol) of 4-tosylamino-4'-nitrodiphenyl sulphide are dissolved in 200 ml of methanol, 50 ml of a 5% strength Raney nickel suspension are added and the mixture is warmed to 35° C. Reduction is carried out after careful addition (evolution of $N_2$) of 5.6 g (0.112 mol) of hydrazine hydrate. The mixture is allowed to after-react at 35° C. for a further 30 minutes and the insoluble material is filtered off. After evaporation of the filtrate in vacuo, the residue is suspended in water and the suspension is extracted with methylene chloride. Drying and evaporation on a rotary evaporator gives the product.

Yield: 12.5 g (75.3% of theory)
Melting point: 135° C.

Example 27

4-Tosylamino-4'-isothiocyanatodiphenyl sulphide

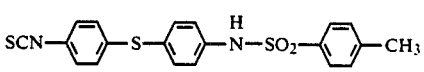

2.5 ml (0.031 mol) of thiophosgene are dissolved in 100 ml of dioxane, the solution is cooled to 0°–5° C. and 10 g (0.027 mol) of 4-tosylamino-4'-aminodiphenyl sulphide, dissolved in 400 ml of dioxane, are slowly added dropwise. 6.2 g≡8.5 ml (0.062 mol) of pyridine are then added and the mixture is allowed to react at 5°–10° C. for a further 3 hours, while stirring. The reaction solution is filtered over silica gel and evaporated to a small volume and the residue is separated by column chromatography (silica gel 60, methylene chloride:methanol=100:1 as the mobile phase). In addition to 1.0 g of 4,4'-di-isothiocyanatodiphenyl sulphide, the desired product is obtained.

Yield: 5.7 g (51.4% of theory)
Melting point: 183° C. (decomposition)

Example 28

4-($\Delta^2$-Thiazolin-2-yl)amino-4'-aminodiphenyl sulphide

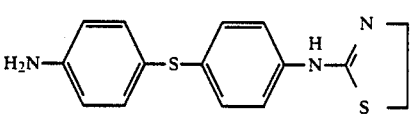

2.8 g (0.0068 mol) of 4-tosylamino-4'-isothiocyanatodiphenyl sulphide are dissolved in 50 ml of methylene chloride, the solution is cooled to 0°–5° C. and 0.4 g≡0.4 ml (0.061 mol) of ethanolamine is added dropwise, with stirring. The mixture is allowed to after-react at room temperature for a further hour and is evaporated to dryness in vacuo and the residue is suspended in concentrated hydrochloric acid. After about 1 hour under reflux, an oily and an aqueous phase are obtained. After being separated off, the aqueous phase is rendered alkaline and a colourless product is obtained.

Yield: 250 mg (12.6% of theory)
Melting point:

Example 29

4-(Δ²-Thiazolin-2-yl)amino-4'-tosylaminodiphenyl sulphide

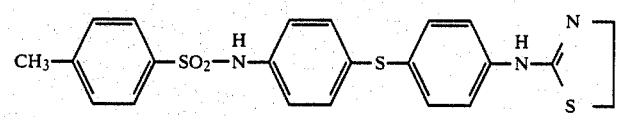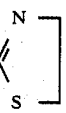

The oil of 4-(Δ²-thiazolin-2-yl)amino-4'-aminodiphenyl sulphide separated off (Example 28) is taken up in methanol and the mixture is rendered alkaline with ammonia solution, while stirring. The product which has precipitated is taken up in methylene chloride and the mixture is washed with water, dried and evaporated to dryness in vacuo.

Yield: 2.2 g (65.7% of theory)
Melting point: >220° C. (decomposition)

Example 30

4-(3-Methyl-thiazolidin-2-yl)imino-4'-tosylaminodiphenyl sulphide

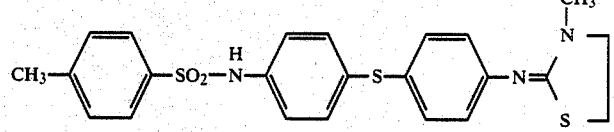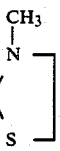

2.8 g (0.0068 mol) of 4-tosylamino-4'-isothiocyanatodiphenyl sulphide (Example 27) are dissolved in 50 ml of methylene chloride, the solution is cooled to 0°–5° C. and 0.5 g≡0.55 ml (0.0068 mol) of N-methylethanolamine is added dropwise. The mixture is allowed to after-react at room temperature for a further hour and the precipitate which has separated out is then filtered off with suction. The still moist product is suspended in 50 ml of concentrated hydrochloric acid and the suspension is heated under reflux for 1 hour. The yellow oil which has separated out is separated off from the aqueous phase and taken up in methanol and the mixture is rendered alkaline with ammonia solution, while stirring. The mixture is concentrated to dryness in vacuo, the residue is taken up in methylene chloride, the mixture is washed with water and the methylene chloride phase is dried and concentrated to dryness.

Yield: 1.8 g (56.5% of theory)
Melting point: >220° C. (decomposition)

Example 31

4,4'-(3,3'-Diacetylthiazolidin-2-yl)diimino-diphenyl sulphide

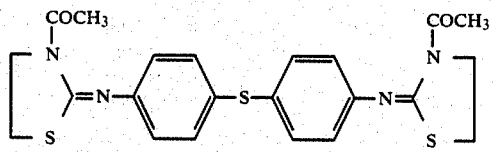

Process variant A:
3.0 g (0.0077 mol) of bis[4-(Δ²-thiazolin-2-yl)aminophenyl]sulphide (Example 2) are dissolved in 50 ml of dried dimethylformamide, and 0.46 g (0.0152 mol) of sodium hydride is added. After the mixture has been allowed to react in an ultrasonic bath for 1 hour, 1.2 ml (0.015 mol) of freshly distilled acetyl chloride are added dropwise at room temperature and the mixture is allowed to after-react for 24 hours. The reaction mixture is then evaporated to dryness in vacuo, the residue is suspended in methylene chloride and the suspension is washed twice with water. Evaporation of the organic phase in a rotary evaporator gives a yellow oil which contains the mono- and diacetylated starting substance. Separation by column chromatography (silica gel 60, methylene chloride:methanol=100:1) gives the desired diactyl product.

Yield: 1.5 g (41% of theory)
Melting point: 120°–122° C.

Process variant B
3.0 g (0.0077 mol) of bis[4-(Δ²-thiazolin-2-yl)aminophenyl]sulphide (Example 2) are dissolved in 100 ml of fresh acetic anhydride and the solution is stirred at

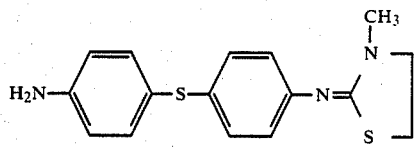

room temperature for 24 hours and poured onto about 300 ml of ice-water. The mixture is extracted three times with methylene chloride and washed with water and the organic phase is dried and evaporated to dryness.

Yield: 2.0 g (54.8% of theory)
Melting point: 120°–122° C.

Example 32

4-(3-Methyl-thiazolidin-2-yl)imino-4'-amino-diphenyl sulphide

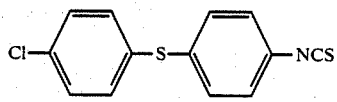

The aqueous phase freed from the yellow oil of 4-(3-methylthiazolidin-2-yl)-imino-4'-tosylaminodiphenyl sulphide (Example 30) is rendered alkaline with aqueous ammonia, whereupon the desired amine precipitates.

Yield: 0.18 g (9.4% of theory)
Melting point: 131°–133° C.

Example 33

4-Chloro-4'-isothiocyanatodiphenyl sulphide

Cl—⟨⟩—S—⟨⟩—NCS 4.2 ml (0.054 mol) of thiophosgene are taken in 50 ml of methylene chloride, a layer of 200 ml of water is introduced under the mixture and the mixture is cooled to 0°-5° C. 12.8 g (0.054 mol) of 4-chloro-4'-aminodiphenyl sulphide in 200 ml of methylene chloride and 4.32 g of NaOH in 50 ml of water are added, with vigorous stirring.

The mixture is then allowed to after-react at 5° C. for a further 2 hours. The organic phase is then separated off, dried and evaporated to dryness in vacuo. The residue is separated by column chromatography (silica gel 60, cyclohexane)

Yield: 14.5 g (98% of theory)
IR (CHCl$_3$): NCS band at 2020 cm$^{-1}$

Example 34

4-($\Delta^2$-Thiazolin-2-yl)amino-4'-chloro-diphenyl sulphide hydrochloride

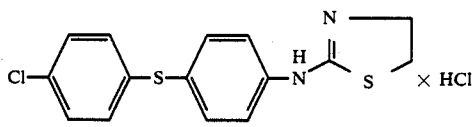

5.0 g (0.018 mol) of 4-chloro-4'-isothiocyanatodiphenyl sulphide are dissolved in 100 ml of methylene chloride, the solution is cooled to 0°-5° C. and 1.1 g 1.1 ml (0.018 mol) of ethanolamine are added dropwise. The mixture is subsequently stirred for 30 minutes, the thiourea which has precipitated is filtered off and the moist product is suspended in concentrated hydrochloric acid. After the suspension has been heated under reflux for 1 hour, the oil is separated off. After some time, the hydrochloride cyrstallizes out of the oil.

Yield: 4.4 g (77.8% of theory)
Melting point: 162° C. (decomposition)

Example 35

4-Methyl-4'-isothiocyanatodiphenyl sulphide

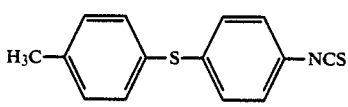

33.8 g 22.4 ml (0.3 mol) of thiophosgene are taken in 100 ml of methylene chloride, a layer of 400 ml of water is introduced under the mixture and 61.5 g (0.3 mol) of 4-amino-4'-methyldiphenyl sulphide in 300 ml of methylene chloride are added dropwise, with vigorous stirring. The mixture is allowed to after-react for 1 hour and the organic phase is separated off, dried and evaporated to dryness in vacuo. The residue is separated by column chromatography (silica gel 60, cyclohexane).

Yield: 58.6 g (76% of theory).

Example 36

4-($\Delta^2$-Thiazolin-2-yl)amino-4'-methyl-diphenyl sulphide

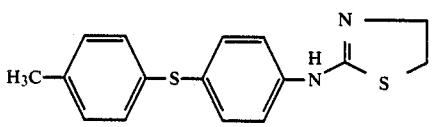

18.0 g (0.07 mol) of 4-methyl-4'-isothiocyanatodiphenyl sulphide are dissolved in 250 ml of methylene chloride, the solution is cooled to 5° C. and 4.3 g=4.5 ml of ethanolamine are added, while stirring. After an after-reaction of 30 minutes, the thiourea is filtered off with suction and suspended in concentrated hydrochloric acid and the suspension is heated under reflux for 1 hour. The oil which has is separated off and taken up in methanol and the desired product is precipitated with ammonia.

Yield: 8.1 g (38.6% of theory)
Melting point: 115° C.

Example 37

4-(5,6-Dihydro-thiazin-2-yl)amino-4'-methyl-diphenyl sulphide hydrochloride

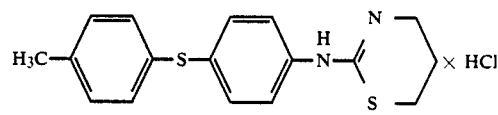

18.0 g (0.07 mol) of 4-methyl-4'-isothiocyanatodiphenyl sulphide (Example 35) are dissolved in 250 ml of methylene chloride, the solution is cooled to 0° to 5° C. and 5.23 g=5.3 ml of 3-aminopropanol are added dropwise. The mixture is subsequently stirred for 30 minutes and the thiourea is filtered off and cyclized by boiling with concentrated hydrochloric acid. The oil which has is taken up in methanol and the desired product is precipitated with ammonia.

Yield: 21.3 g (97% of theory)
Melting point: 85°-87° C.

Example 38

4-Methyl-4'-(3-methylthiazolidin-2-yl)imino-diphenyl sulphide

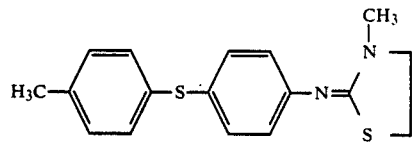

18.0 g (0.07 mol) of 4-methyl-4'-isothiocyanatodiphenyl sulphide (Example 35) are dissolved in 250 ml of methylene chloride, the solution is cooled to 0° to 5° C. and 5.3 g=5.5 ml of N-methylethanolamine are added dropwise. The mixture is allowed to after-react for 30 minutes and the thiourea is filtered off and cyclized by boiling with concentrated hydrochloric acid. The oil which has precipitated is taken up in methanol and the desired product is precipitated with ammonia.

Yield: 18.3 g (83.3% of theory)
Melting point: 59°-61° C.

Example 39

4-Amino-4-thiazol-2-yl-amino-diphenyl sulphide

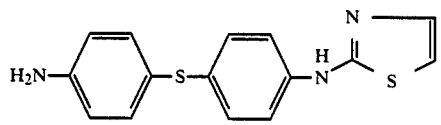

4.0 g (0.012 mol) of 4-nitro-4'-thiazol-2-yl-aminodiphenyl sulphide (Example 48) and 1.5 g (0.03 mol) of hydrazine hydrate are dissolved in 50 ml of methanol/tetrahydrofuran (1:1), and Raney nickel in methanol is added in small portions at room temperature, while stirring. The reaction mixture warms slightly, with evolution of gas. The mixture is then warmed under reflux for 3 hours, the insoluble material is filtered off, the filtrate is concentrated to dryness in vacuo and the residue is separated by column chromatography (silica gel 60, methylene chloride:tetrahydrofuran=9:1).

Yield: 3.3 g (92% of theory)
Melting point: 119° C.

Example 40

4-Isothiocyanato-4'-thiazol-2-yl-amino-diphenyl sulphide

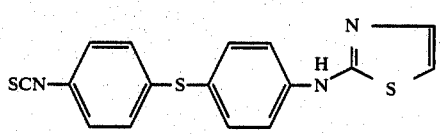

1.3 g (0.01 mol) of thiophosgene are dissolved in 10 ml of methylene chloride, a layer of 20 ml of water is introduced under the mixture and 3.0 g (0.01 mol) of 4-amino-4-thiazol-2-yl-aminodiphenyl sulphide (Example 39) in 50 ml of methylene chloride/tetrahydrofuran (1:1) are added dropwise. 10 ml of 2N sodium hydroxide solution are then added dropwise at room temperature, with vigorous stirring, and the mixture is subsequently stirred for a further 2 hours. The dark red organic phase is separated off and subjected to column chromatography (silica gel 60, methylene chloride:cyclohexane=1:1).

Yield: 3.2 g (93.6% of theory)
Melting point: 134° C.

Example 41

4-($\Delta^2$-Thiazolin-2-yl)-amino-4'-thiazol-2-yl-amino-diphenyl sulphide

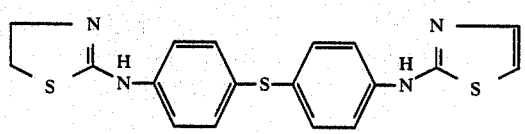

3.2 g (0.0094 mol) of the isocyanate from Example 40 are dissolved in 50 ml of methylene chloride, and 0.6 g=0.6 ml (0.0094 mol) of ethanolamine is added dropwise. The red color of the sulphide disappears suddenly. The mixture is evaporated to dryness, the residue is suspended in concentrated hydrochloric acic and the suspension is heated under reflux for 1 hour. The batch is diluted with water and the end product is precipitated with 2N sodium hydroxide solution. The product is then separated by column chromatography (silica gel 60, glacial acetic acid/methanol/methylene chloride=10/5/85).

Yield: 2.2 g (61% of theory)
Melting point: 182° C.

Example 42

4-Nitro-4'-isothiocyanato-diphenyl sulphide

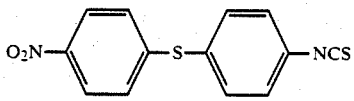

12 g=7.9 ml (0.1 mol) of thiophosgene are dissolved in 100 ml of methylene chloride, a layer of 200 ml of water is introduced underneath the mixture and a solution of 24.6 g (0.1 mol) of 4-amino-4'-nitro-diphenyl sulphide in 250 ml of methylene chloride and 8 g (0.2 mol) of NaOH in 50 ml of water are added at 0°-5° C., with vigorous stirring. The mixture is allowed to after-react at 0°-5° C. for a further 2 hours, the organic phase is separated off and evaporated to dryness and the residue is subjected to column chromatography (silica gel 60, cyclohexane).

Yield: 28.1 g (99.6% of theory)
Melting point: 109° C.

Example 43

4-Nitro-4'-($\Delta^2$-thiazolin-2-yl)amino-diphenyl sulphide

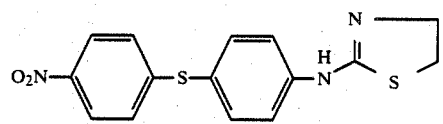

28 g (0.1 mol) of the above isothiocyanate (Example 42) are dissolved in 300 ml of methylene chloride, the solution is cooled to 0°-5° C. and 5.9 g 5.9 ml (0.1 mol) of ethanolamine are added dropwise. After further stirring for 1 hour, the thiourea is filtered off with suction, the residue is suspended in concentrated hydrochloric acid and the suspension is heated under reflux for 1 hour. The oil which has is taken up in methanol and the product is precipitated with ammonia.

Yield: 28 g (84.6% of theory)
Melting point: 178° C.

Example 44

4-Nitro-4'-(3-trifluoromethylphenyl)sulphonaminodiphenyl sulphide

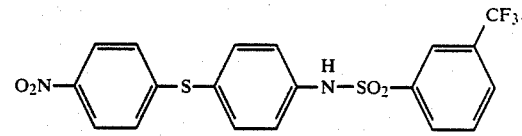

25.1 g (0.1 mol) of 4-amino-4'-nitrodiphenyl sulphide are dissolved in 1,500 ml of dioxane, 8 ml (0.1 mol) of pyridine are added and 24.5 g (0.1 mol) of 3-trifluoromethylbenzenesulphonyl chloride are added dropwise, while stirring. The mixture is allowed to after-react at room temperature for 48 hours and is evaporated to dryness in vacuo, the residue is taken up in ethyl acetate, the mixture is washed neutral with water and dried and the solvent is evaporated off.

Yield: 24.5 g (54% of theory)
Melting point: 113° C.

Example 45

4-Amino-4'-(3-trifluoromethylphenyl)sulphonylaminodiphenyl sulphide

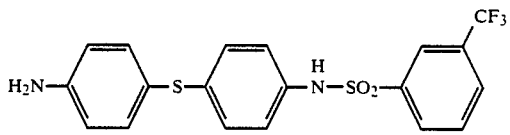

24.4 g (0.054 mol) of the nitro compound from Example 44 are dissolved in 300 ml of methanol, 6.7 g≡6.5 ml (0.135 mol) of hydrazine hydrate and, gradually, 25 ml of 5% strength Raney nickel suspension are added and the mixture is warmed under reflux. The mixture is allowed to after-react for a further 30 minutes until no further $N_2$ is evolved. After removal of the insoluble material by filtration, the filtrate is concentrated to dryness in vacuo and the residue is taken up in methylene chloride. The mixture is washed twice with water and extracted with hydrochloric acid. After rendering alkaline with sodium hydroxide solution, the mixture is extracted with methylene chloride and the extract is dried with $Na_2SO_4$ and evaporated to dryness in vacuo. The residue is subjected to column chromatography (silica gel 60, methylene chloride).
Yield: 6.3 g (27.5% of theory)
Melting point: 133° C.

Example 46

4-Isothiocyanato-4'-(3-trifluoromethylphenyl)sulphonylamino-diphenyl sulphide

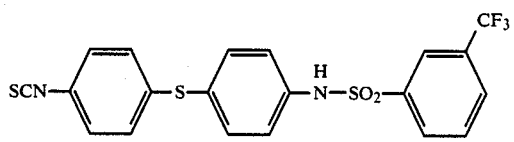

1.50 g≡1.1 ml (0.013 mol) of thiophosgene are dissolved in 50 ml of methylene chloride, a layer of 20 ml of water is introduced under the mixture and the mixture is cooled to 0°–5° C. 5.7 g (0.013 mol) of the amine from Example 45 in 100 ml of methylene chloride are added dropwise, with vigorous stirring. After an after-reaction of 30 minutes, the organic phase is separated off, dried and evaporated to dryness in vacuo. Separation by column chromatography is then carried out (silica gel 60, methylene chloride).
Yield: 5.2 g (85.8% of theory)
Melting point: 93° C.

Example 47

4-(Δ²-Thiazolin-2-yl)amino-4'-(3-trifluoromethylphenyl)sulphonylamino-diphenyl sulphide

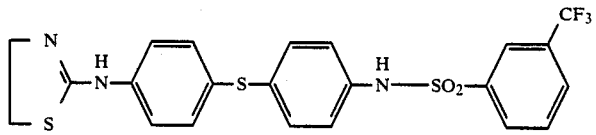

5.2 g (0.011 mol) of the isothiocyanate from Example 46 are dissolved in 100 ml of methylene chloride, and 0.08 g≡0.08 ml (0.011 mol) of ethanolamine is added at 0°–5° C., while stirring. The mixture is allowed to after-react for 30 minutes, the thiourea is filtered off and suspended in concentrated hydrochloric acid and the suspension is heated at the boiling point for 1 hour. The oil which is separated off from the aqueous phase and the thiazoline is precipitated with ammonia.
Yield: 5.1 g (91.1% of theory)
Melting point: 182° C.

Example 48

N-[4-(4-Nitrophenylthio)phenyl]thiourea

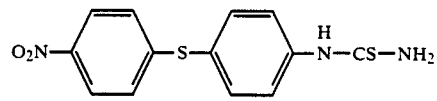

24.6 g (0.1 mol) of 4-nitro-4'-aminodiphenyl sulphide are dissolved in 150 ml of methylene chloride, a layer of 100 ml of water is introduced under the mixture and 12.7 g≡8.4 ml (0.11 mol) of thiophosgene in 50 ml of methylene chloride are added, with vigorous stirring. 50 ml of 2N sodium hydroxide solution are added dropwise, gentle warming occurring (30°–35° C.). After the mixture has been stirred at room temperature for 3 hours, the organic phase is separated off and 25% strength ammonia solution is added. The reaction mixture is stirred overnight and the thiourea is filtered off.
Yield: 25.1 g (83% of theory)
Melting point: 149° C.

Example 49

4-Nitro-4'-thiazol-2-yl-amino-diphenyl sulphide

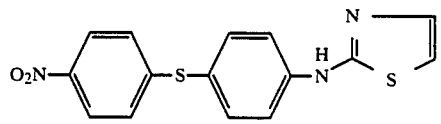

6.1 g (0.002 mol) of the thiourea from Example 48 are suspended in 20 ml of water and 5.8 g≡5 ml (0.04 mol) of 1-chlorodiethyl ether (85% pure) are added. A clear solution thereby forms, and warms gently. The solution is heated at 80° C. for a further hour and is allowed to cool and is neutralized with $NaHCO_3$ solution. The precipitate which has separated out is filtered off with suction and dried.
Yield: 4.7 g (72% of theory)
Melting point: 159° C.

The following compounds were prepared analogously to Example 49:

Example 50

Bis[4,4'-(bisthiazol-2-yl)amino]diphenyl sulphide

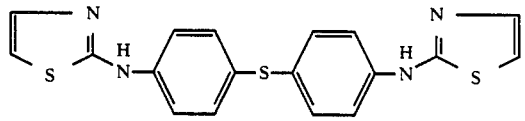

Example 51

4-(Thiazol-2-yl)amino-diphenyl sulphide

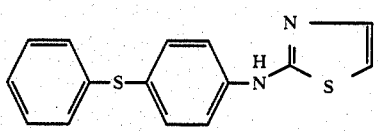

Yield: 71% of theory (based on $H_5C_6$—S—$C_6H_5$—$NHCSNH_2$)
Melting point: 128° C.

Example 52

4-(4-Methyl-thiazol-2-yl)amino-diphenyl sulphide

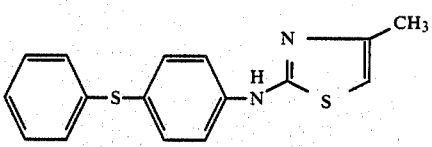

Yield: 64% of theory (based on $H_5C_6$—S—$C_6H_5$—$NHCSNH_2$)
Melting point: 112° C.

The following compounds were prepared analogously to Example 3:

Example 53

Bis[4-($\Delta^2$-thiazolin-2-yl)aminophenyl]sulphide lactate

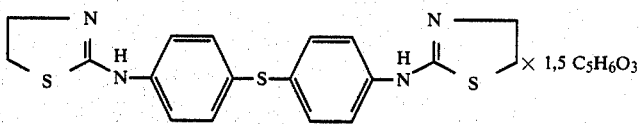

Example 54

Bis[4-($\Delta^2$-thiazolin-2-yl)aminophenyl]sulphide sulphate

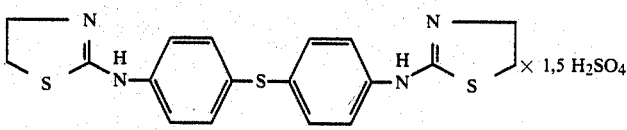

Example 55

Bis[4-($\Delta^2$-thiazolin-2-yl)aminophenyl]sulphide citrate

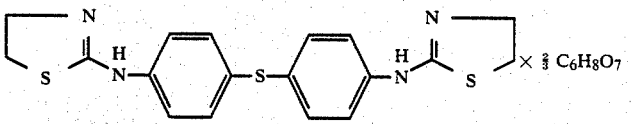

Use Example

The pharmacological action of the substances according to the invention was determined by the following method:

The leucotriene B4 (LTB4) formed after stimulation with Ca-ionophor is determined by means of reversed phase HPLC in accordance with the method of Borgeat et al. *Proc. Natl. Acad. Sci. USA*, 76, 215 (1982) as a measure of the lipoxygenase activity of PMN in rats.

The $IC_{50}$ values determined for the following compounds by this test, for example, are listed in Table 1.

TABLE 1

| Example No. | $IC_{50}$ values [g/ml] |
|---|---|
| 2 | $1.35 \cdot 10^{-7}$ |
| 3 | $3.0 \cdot 10^{-7}$ |
| 4 | $2.7 \cdot 10^{-7}$ |
| 10 | $7.5 \cdot 10^{-8}$ |
| 12 | $2.8 \cdot 10^{-8}$ |
| 17 | $1.1 \cdot 10^{-7}$ |
| 22 | $5.1 \cdot 10^{-8}$ |
| 29 | $6.6 \cdot 10^{-8}$ |

It will be appreciated that the instant specification and claims are set forth by way of illustration and not limitation, and that various modifications and changes may be made without departing from the spirit and scope of the present invention.

We claim:

1. A diaryl sulphide derivative of the formula

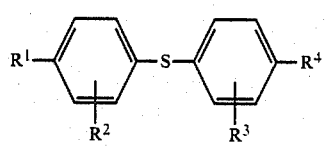

in which $R^1$ represents a radical of the formulae

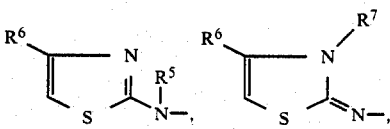

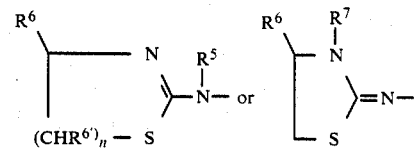

wherein
- $R^5$ represents hydrogen, alkyl having 1 to 12 carbon atoms, aralkyl, said aralkyl having an aryl radical with 7 to 14 carbon atoms which is bonded via an alkylene chain, wherein there are 1 to 6 carbon atoms in the aliphatic aromatic part of said aralkyl, or acyl, said acyl representing phenyl or straight-chain or branched lower alkyl with 1 to 6 carbon atoms, which are bonded via a carbonyl group,
- $R^5$ and $R^{6'}$ are identical or different and represent hydrogen, alkyl having 1 to 12 carbon atoms, aralkyl or aryl having 6 to 12 carbon atoms,
- $R^7$ represents alkyl having 1 to 12 carbon atoms, cycloalkyl, aralkyl, acyl, said acyl representing phenyl or straight-chain or branched lower alkyl with 1 to 6 carbon atoms, which are bonded via a carbonyl group, or aryl having 6 to 12 carbon atoms and
- n represents the number 1 or 2,
- $R^2$ and $R^3$ are identical or different and represent hydrogen, alkyl having 1 to 12 carbon atoms, alkenyl, cycloalkyl, alkoxy, alkylthio, halogenoalkyl, halogenoalkoxy, halogenoalkylthio, aryl having 6 to 12 carbon atoms, aralkyl, aryloxy, aralkoxy, aralkylthio, acyl, said acyl representing phenyl or straight-chain or branched lower alkyl with 1 to 6 carbon atoms, which are bonded via a carbonyl group, carboxyl, alkoxycarbonyl, carboxyalkyl, alkoxycarbonylalkyl, nitro, cyabo or halogen, or represent a group of the formula

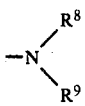

wherein
- $R^8$ and $R^9$ are identical or different and represent hydrogen, alkyl having 1 to 12 carbon atoms, aryl having 6 to 10 carbon atoms, aralkyl, acyl, said acyl representing phenyl or straight-chain or branched lower alkyl with 1 to 6 carbon atoms, which are bonded via a carbonyl group, trifluoroacetyl, alkylsulphonyl, arylsulphonyl, trifluoromethylphenylsulphonyl or tolylsulphonyl and
- $R^4$ has one of the abovementioned meanings of $R^1$, or represents hydrogen, alkyl having 1 to 12 carbon atoms, alkenyl, cycloalkyl, alkoxy, alkylthio, halogenoalkyl, halogenoalkoxy, halogenoalkylthio, aryl having 6 to 10 carbon atoms, aralkyl, aryloxy, aralkoxy, aralkylthio, acyl, said acyl representing phenyl or straight-chain or branched lower alkyl with 1 to 6 carbon atoms, which are bonded via a carbonyl group, carboxyl, alkoxycarbonyl, carboxyalkyl, alkoxycarbonylalkyl, nitro, cyano or halogen, or represents a group of the formula

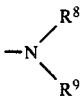

wherein
- $R^8$ and $R^9$ have the abovementioned meanings and salts thereof.

2. A diaryl sulphide derivative according to claim 1, wherein
- $R^1$ represents a thiazolamino radical of the formulae

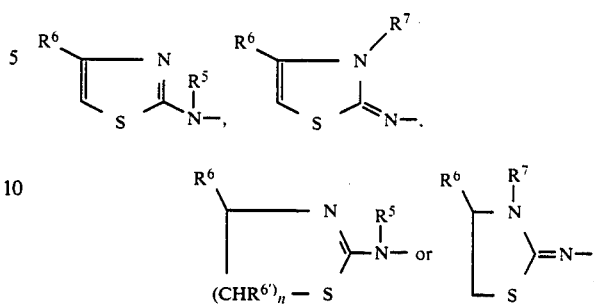

wherein
- $R^5$ represents hydrogen, lower alkyl, benzyl, benzoyl or acetyl,
- $R^6$ and $R^{6'}$ are identical or different and represent hydrogen, lower alkyl or phenyl,
- $R^7$ represents lower alkyl, cyclohexyl, benzyl, acetyl, benzoyl or phenyl and
- n represents the number 1 or 2,
- $R^2$ and $R^3$ are identical or different and represent hydrogen, lower alkyl, lower alkenyl, lower alkoxy, lower alkylthio, halogeno-lower alkyl, halogeno-lower alkoxy, trifluoromethylthio, phenyl, benzyl, phenoxy, benzyloxy, lower alkylcarbonyl, benzoyl, carboxyl, lower alkoxycarbonyl, carboxy-lower alkyl, lower alkoxycarbonyl-lower alkyl, nitro, cyano, fluorine, chlorine or bromine, or represent the group of the formula

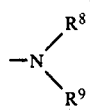

wherein
- $R^8$ and $R^9$ are identical or different and represent hydrogen, lower alkyl, phenyl, benzyl, lower alkylcarbonyl, benzoyl, trifluoroacetyl, lower alkylsulphonyl, phenylsulphonyl, trifluoromethylphenylsulphonyl or tolylsulphonyl, and
- $R^4$ has one of the abovementioned meanings of $R^1$, or represents hydrogen, lower alkyl, lower alkenyl, lower alkoxy, lower alkylthio, halogeno-lower alkyl, halogeno-lower alkoxy, trifluoromethylthio, phenyl, benzyl, phenoxy, benzyloxy, lower alkylcarbonyl, benzoyl, carboxyl, lower alkoxycarbonyl, carboxy-lower alkyl, lower alkoxy-lower alkyl, nitro, cyano, fluorine, chlorine or bromine, or represents a group of the formula

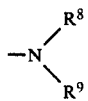

wherein
- $R^8$ and $R^9$ have the abovementioned meanings, and salts thereof.

3. A diaryl sulphide derivative according to claim 1, wherein
- $R^1$ represents a thiazolamino radical of the formulae

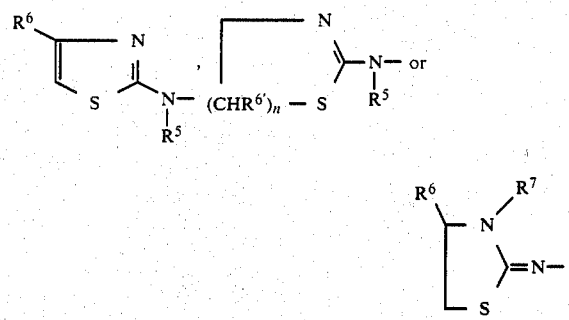

wherein
- $R^5$ represents hydrogen, methyl, ethyl, propyl, isopropyl, benzyl or acetyl, and
- $R^6$ and $R^{6'}$ are identical or different and represent hydrogen, methyl, ethyl, propyl, isopropyl, butyl, isobutyl or phenyl and
- $R^7$ represents methyl, ethyl or acetyl,
- $R^2$ and $R^3$ are identical or different and represent hydrogen, methyl, ethyl, propyl, isopropyl, allyl, methoxy, methylthio, trifluoromethyl, trifluoromethoxy, difluoromethyl, trifluoromethylthio, acetyl, carboxyl, carboxymethyl, methoxycarbonyl, ethoxycarbonyl, methoxycarbonylmethyl, 1-methoxycarbonyl-ethyl, 2-ethoxycarbonyl-ethyl, 2-ethoxycarbonyl-ethyl, cyano, fluorine, chlorine or bromine,
- $R^4$ has one of the abovementioned meanings of $R^1$, or represents hydrogen, methyl, ethyl, propyl, isopropyl, butyl, tert.-butyl, methoxy, methylthio, trifluoromethyl, trifluoromethoxy, trifluoromethylthio, acetyl, carboxyl, methoxycarbonyl, ethoxycarbonyl, carboxymethyl, methoxycarbonyl-methyl, ethoxycarbonyl-methyl, 1-methoxycarbonyl-ethyl, 2-methoxycarbonyl-ethyl, 1-ethoxycarbonyl-ethyl, 2-ethoxycarbonyl-ethyl, nitro, cyano, fluorine, chlorine, bromine or a group of the formula

wherein
- $R^8$ and $R^9$ are identical or different and represent hydrogen, methyl, ethyl, propyl, isopropyl, phenyl, benzyl, acetyl, trifluoroacetyl, methylsulphonyl, phenylsulphonyl or trifluoromethylphenylsulphonyl, toluylsulphonyl, and salts thereof.

4. A diaryl sulphide derivative according to claim 1, said diaryl sulphide derivative is selected from the group consisting of bis-[4-($\Delta^2$-thiazolin-2-yl)aminophenyl]sulphide, bis-[4-(4-phenyl-$\Delta^2$-thiazolin-2-yl)aminophenyl]sulphide, [2-phenylthio-5-($\Delta^2$-thiazolin-2-yl)amino]phenylacetic acid, methyl[2-phenylthio-5-($\Delta^2$-thiazolin-2-yl)amino]phenylacetate, bis-[4-(5-methyl-$\Delta^2$-thiazolin-2-yl)aminophenyl]sulphide, bis-[4-(4-methyl-$\Delta^2$-thiazidin-2-yl)aminophenyl]sulphide, 4-($\Delta^2$-thiazolin-2-yl)amino-4'-aminodiphenyl sulphide, 4-($\Delta^2$-thiazolin-2-yl)amino-4'-tosylaminodiphenyl sulphide, 4-(3-methylthiazolidin-2-yl)imino-4'-tosylaminodiphenyl sulphide, 4,4'-(3,3'-diacetylthiazolidin-2-yl)diiminodiphenyl sulphide, 4-(3-methylthiazolidin-2-yl)imino-4'-amino-diphenyl sulphide, 4-($\Delta^2$-thiazolin-2-yl)amino-4'-chloro-diphenyl sulphide hydrochloride, 4-($\Delta^2$-thiazolin-2-yl)amino-4'-methyl-diphenyl sulphide, 4-methyl-4'-(3-methylthiazolidin-2-yl)imino-diphenyl sulphide, 4-($\Delta^2$-thiazolin-2-yl)amino-4'-thiazol-2-yl-amino-diphenyl sulphide, 4-nitro-4'-($\Delta^2$-thiazol-2-yl)amino-diphenyl sulphide, 4-($\Delta^2$-thiazolin-2-yl)amino-4'-(3-trifluoromethylphenyl)-sulphonylamino-diphenyl sulphide and bis-[4-(5-methyl-$\Delta^2$-thiazolin-2-yl)aminophenyl]sulphide.

5. A medicament comprising an enzymatically inhibiting amount of a diaryl sulphide derivative according to claim 1 in admixture with a pharmaceutically acceptable excipient of solvent, said amount being sufficient to inhibit enzymatic reactions in the context of arachidonic acid metabolism.

6. A medicament according to claim 5, wherein the diaryl sulphide derivative is contained in an amount of 0.5 to 90% by weight.

7. A unit dose of a medicament according to claim 5 in the form of a tablet, capsule, caplet or pill.

8. A method of inhibiting enzymatic reactions in the context of arachidonic acid metabolism in a patient comprising administering to said patient an effective amount of a diaryl sulphide derivative according to claim 1.

* * * * *

UNITED STATES PATENT AND TRADEMARK OFFICE
CERTIFICATE OF CORRECTION

PATENT NO. : 4,771,062
DATED : September 13, 1988
INVENTOR(S) : Siegfried Raddatz, et al It is certified that error appears in the above-identified patent and that said Letters Patent is hereby corrected as shown below:

| | |
|---|---|
| Title Page, under "U.S. Patent Documents", line 4 | Correct spelling of --Neumann-- |
| Col. 12, line 56 | Correct spelling of --Encyclopedia-- |
| Col. 13, line 59 | Delete "aryl" and substitute --acyl-- |
| Col. 27, line 28 | Delete "4-(4-(4-cyano-" and substitute --(4-(4-cyano- -- |
| Col. 32, line 68 | After "Melting point:" insert --148°C-- |
| Col. 34, line 17 | Delete "diactyl" and substitute --diacetyl-- |
| Col. 36, lines 5, 27 and Col. 38, line 38 | After "The oil which has" insert --precipitated-- |
| Col. 36, line 24 | Delete "5.23" and substitute --5.3-- |
| Col. 37, line 56 | Delete "acic" and substitute --acid-- |
| Col. 39, line 38 | Delete "1.50" and substitute --1.59-- |
| Col. 41, lines 35, 45 | Delete "1,5" and substitute --1.5-- |
| Col. 43, line 29 | Delete "cyabo" and substitute --cyano-- |
| Col. 46, line 34 | Before "solvent" change "of" to --or-- |

Signed and Sealed this

Ninth Day of May, 1989

Attest:

DONALD J. QUIGG

Attesting Officer    Commissioner of Patents and Trademarks